United States Patent
Nakayama

(10) Patent No.: US 12,127,862 B2
(45) Date of Patent: Oct. 29, 2024

(54) IMAGE PROCESSING DEVICE, IMAGING CONTROL DEVICE, RADIOGRAPHY SYSTEM, IMAGE PROCESSING METHOD, AND IMAGE PROCESSING PROGRAM

(71) Applicant: FUJIFILM CORPORATION, Tokyo (JP)

(72) Inventor: Hiroki Nakayama, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 506 days.

(21) Appl. No.: 17/591,571

(22) Filed: Feb. 2, 2022

(65) Prior Publication Data

US 2022/0273249 A1    Sep. 1, 2022

(30) Foreign Application Priority Data

Feb. 26, 2021    (JP) .................................. 2021-031246

(51) Int. Cl.
*A61B 6/02*    (2006.01)
*A61B 6/00*    (2024.01)
(Continued)

(52) U.S. Cl.
CPC ................ *A61B 6/025* (2013.01); *A61B 6/03* (2013.01); *A61B 6/502* (2013.01); *A61B 6/5205* (2013.01)

(58) Field of Classification Search
CPC ........... A61B 6/025; A61B 6/03; A61B 6/502; A61B 6/5205; A61B 6/4007; G06T 2211/436; G06T 11/006
See application file for complete search history.

(56) References Cited

U.S. PATENT DOCUMENTS

2014/0093029 A1    4/2014 Masumoto et al.
2015/0036796 A1    2/2015 Dornberger et al.
(Continued)

FOREIGN PATENT DOCUMENTS

EP    2608530 A2    6/2013
JP    2013-150304 A    8/2013
(Continued)

OTHER PUBLICATIONS

English language translation of the following: Office action dated Apr. 23, 2024 from the JPO in a Japanese patent application No. 2021-031246 corresponding to the instant patent application. This office action translation is submitted now in order to supplement the understanding of the cited references which are being disclosed in the instant Information Disclosure Statement.

(Continued)

*Primary Examiner* — Courtney D Thomas
(74) *Attorney, Agent, or Firm* — SOLARIS Intellectual Property Group, PLLC

(57) ABSTRACT

A CPU acquires a projection image group obtained by tomosynthesis imaging in an irradiation angle range wider than an overall imaging irradiation angle range. The CPU generates a plurality of first tomographic images including a part of the breast, using projection images obtained by the tomosynthesis imaging in a first irradiation angle range wider than the overall imaging irradiation angle range, and generates a plurality of second tomographic images including the entire breast, using projection images obtained by the tomosynthesis imaging in a second irradiation angle range that is equal to or narrower than the overall imaging irradiation angle range.

16 Claims, 11 Drawing Sheets

(51) Int. Cl.
   *A61B 6/03*  (2006.01)
   *A61B 6/50*  (2024.01)

(56) References Cited

U.S. PATENT DOCUMENTS

| | | | |
|---|---|---|---|
| 2015/0052471 A1 | 2/2015 | Chen et al. | |
| 2016/0256125 A1* | 9/2016 | Smith | G06T 11/006 |
| 2017/0281131 A1 | 10/2017 | Sendai | |
| 2018/0047211 A1 | 2/2018 | Chen et al. | |
| 2020/0100749 A1 | 4/2020 | Makino et al. | |
| 2020/0146645 A1 | 5/2020 | Nakayama | |
| 2021/0030373 A1 | 2/2021 | Arai | |
| 2021/0030384 A1 | 2/2021 | Arai | |

FOREIGN PATENT DOCUMENTS

| | | |
|---|---|---|
| JP | 2014-068752 A | 4/2014 |
| JP | 2015-506794 A | 3/2015 |
| JP | 2016-532474 A | 10/2016 |
| JP | 2017-176509 A | 10/2017 |
| JP | 2018-047256 A | 3/2018 |
| JP | 2018-057694 A | 4/2018 |
| JP | 2020-048993 A | 4/2020 |
| JP | 2020-137873 A | 9/2020 |
| JP | 2021-019930 A | 2/2021 |
| JP | 2021-019931 A | 2/2021 |
| WO | 2015054518 A1 | 4/2015 |
| WO | 2015/147008 A1 | 10/2015 |
| WO | 2019/017442 A1 | 1/2019 |

OTHER PUBLICATIONS

Extended European Search Report dated Jul. 27, 2022, issued in corresponding EP Patent Application No. 22154950.4.

* cited by examiner

IMAGE PROCESSING DEVICE, IMAGING CONTROL DEVICE, RADIOGRAPHY SYSTEM, IMAGE PROCESSING METHOD, AND IMAGE PROCESSING PROGRAM

CROSS-REFERENCE TO RELATED APPLICATIONS

The present application claims priority under 35 U.S.C. § 119 to Japanese Patent Application No. 2021-031246 filed on Feb. 26, 2021. The above application is hereby expressly incorporated by reference, in its entirety, into the present application.

BACKGROUND

1. Technical Field

The present disclosure relates to an image processing device, an imaging control device, a radiography system, an image processing method, and an image processing program.

2. Description of the Related Art

In general, so-called tomosynthesis imaging is known which irradiates an object with radiation emitted from a radiation source at each of a plurality of irradiation positions having different irradiation angles to capture a plurality of radiographic images of the object at different irradiation positions.

In the tomosynthesis imaging, as an irradiation angle range, which is the range of irradiation angles at a plurality of irradiation positions where imaging is performed, becomes wider, the resolution of a tomographic image generated using the obtained plurality of projection images becomes higher. However, a region irradiated with radiation varies depending the irradiation angle due to the influence of the oblique incidence of the radiation. Therefore, as the irradiation angle becomes larger, the irradiation region is more likely to be affected by the oblique incidence of the radiation, and an object region included in the projection image becomes smaller. In the generation of a tomographic image from a plurality of projection images, in a case in which an object region reconstructed as the tomographic image is referred to as a reconstructed region, the reconstructed region becomes narrower as the irradiation angle range becomes wider. The reason is that the reconstruction needs to be performed using a plurality of projection images obtained by imaging the same region of the object while changing the irradiation angle and the reconstructed region is limited to the region of the subject which is common to all of the plurality of projection images used for the reconstruction. Therefore, as the irradiation angle becomes larger, the region of the object included in the projection image becomes narrower. As a result, as the irradiation angle range becomes wider, the reconstructed region becomes narrower. On the contrary, as the irradiation angle range becomes narrower, the irradiation region is more unlikely to be affected by the oblique incidence of the radiation on the object. Therefore, the reconstructed region becomes wide.

That is, as the irradiation angle range becomes wider, the reconstructed region is more limited to a part of the object, but the resolution of the tomographic image becomes higher. As the irradiation angle range becomes narrower, the reconstructed region becomes wider to include the entire object, but the resolution of the tomographic image becomes lower.

Therefore, a technique is known which performs tomosynthesis imaging while changing the irradiation angle range. For example, JP2020-137873A discloses a technique that performs two types of tomosynthesis imaging in a standard mode and a high-resolution mode in which an irradiation angle range is wider than that in the standard mode.

SUMMARY

In the above-mentioned technique according to the related art, a tomographic image is generated from a projection image group obtained by the tomosynthesis imaging in the standard mode in order to obtain two types of tomographic images having different reconstructed regions and resolutions. In addition, a tomographic image is generated from a projection image group obtained by the tomosynthesis imaging in the high-resolution mode.

As described above, in the technique according to the related art, the tomographic image is generated from each of the projection image groups obtained by each tomosynthesis imaging operation.

The present disclosure has been made in view of the above-mentioned problems, and an object of the present disclosure is to provide an image processing device, an imaging control device, a radiography system, an image processing method, and an image processing program that can generate a high-resolution tomographic image and a tomographic image including the entire object from a projection image group including a plurality of projection images obtained by tomosynthesis imaging in an irradiation angle range in which the entire object is not included in the tomographic image in a case in which the tomographic image is generated using all of the projection images.

In order to achieve the above object, according to a first aspect of the present disclosure, there is provided an image processing device that is used in a radiography apparatus performing tomosynthesis imaging which irradiates an object with radiation emitted from a radiation source at each of a plurality of irradiation positions having different irradiation angles to capture projection images of the object at each of the irradiation positions. The image processing device comprises at least one processor. The processor acquires a projection image group including a plurality of projection images obtained by the tomosynthesis imaging in an irradiation angle range wider than an overall imaging irradiation angle range in which a tomographic image including an entire object is obtainable in a case in which the tomographic image is generated using the projection images obtained at each of the plurality of irradiation positions, generates a plurality of first tomographic images including a part of the object, using a plurality of projection images obtained by the tomosynthesis imaging in a first irradiation angle range wider than the overall imaging irradiation angle range among the projection images included in the projection image group, and generates a plurality of second tomographic images including the entire object, using a plurality of projection images obtained by the tomosynthesis imaging in a second irradiation angle range that is equal to or narrower than the overall imaging irradiation angle range among the projection images included in the projection image group.

According to a second aspect of the present disclosure, in the image processing device according to the first aspect, the processor may acquire a plurality of projection images obtained by one tomosynthesis imaging operation as the projection image group.

According to a third aspect of the present disclosure, in the image processing device according to the first aspect or the second aspect, the processor may generate the plurality of second tomographic images using some of the plurality of projection images used to generate the first tomographic images.

According to a fourth aspect of the present disclosure, in the image processing device according to any one of the first to third aspects, the processor may display the first tomographic image and the second tomographic image side by side.

According to a fifth aspect of the present disclosure, in the image processing device according to any one of the first to fourth aspects, the processor may display information indicating a range of the object included in the first tomographic image so as to be superimposed on the second tomographic image.

According to a sixth aspect of the present disclosure, in the image processing device according to any one of the first to third aspects, the processor may generate at least one of a first composite two-dimensional image obtained by combining at least some of the plurality of first tomographic images or a second composite two-dimensional image obtained by combining at least some of the plurality of second tomographic images and may display at least one of the plurality of first tomographic images or the first composite two-dimensional image and at least one of the plurality of second tomographic images or the second composite two-dimensional image side by side.

According to a seventh aspect of the present disclosure, in the image processing device according to any one of the first to third aspects, the processor may generate a second composite two-dimensional image obtained by combining at least some of the plurality of second tomographic images and may display information indicating a range of the object included in the first tomographic image so as to be superimposed on the second composite two-dimensional image.

According to an eighth aspect of the present disclosure, in the image processing device according to any one of the first to seventh aspects, the processor may set a slice thickness of the plurality of first tomographic images to be smaller than a slice thickness of the plurality of second tomographic images.

According to a ninth aspect of the present disclosure, in the image processing device according to any one of the first to eighth aspects, the processor may acquire overall imaging information indicating the overall imaging irradiation angle range which is determined on the basis of at least one of a thickness of the object or an area of the object and may specify the second irradiation angle range on the basis of the acquired overall imaging information.

According to a tenth aspect of the present disclosure, in the image processing device according to the ninth aspect, the object may be a breast that is placed on an imaging table and is compressed by a compression member, and the area of the object is a contact area of the breast with the imaging table or a contact area of the breast with the compression member.

According to an eleventh aspect of the present disclosure, in the image processing device according to any one of the first to tenth aspects, the radiation source may include a plurality of radiation tubes that are disposed at each of the plurality of irradiation positions and generate the radiation, and the radiography apparatus may sequentially generate the radiation from the plurality of radiation tubes to perform the tomosynthesis imaging.

According to a twelfth aspect of the present disclosure, in the image processing device according to any one of the first to tenth aspects, the radiation source may include a radiation tube that generates the radiation, and the radiography apparatus may move the radiation source to the plurality of irradiation positions to perform the tomosynthesis imaging.

Further, in order to achieve the above object, according to a thirteenth aspect of the present disclosure, there is provided an imaging control device that is used in a radiography apparatus performing tomosynthesis imaging which irradiates an object with radiation emitted from a radiation source at each of a plurality of irradiation positions having different irradiation angles to capture projection images of the object at each of the irradiation positions. The imaging control device comprises at least one processor. The processor acquires overall imaging information indicating an overall imaging irradiation angle range determined on the basis of at least one of a thickness of the object or an area of the object and controls the radiography apparatus such that the tomosynthesis imaging is performed in an irradiation angle range wider than the overall imaging irradiation angle range corresponding to the acquired overall imaging information.

Furthermore, in order to achieve the above object, according to a fourteenth aspect of the present disclosure, there is provided a radiography system comprising: a radiation source that generates radiation; a radiography apparatus that performs tomosynthesis imaging which irradiates an object with the radiation emitted from the radiation source at each of a plurality of irradiation positions having different irradiation angles to capture projection images of the object at each of the irradiation positions; and the image processing device according to the present disclosure.

Moreover, in order to achieve the above object, according to a fifteenth aspect of the present disclosure, there is provided an image processing method that is executed by a computer and is used in a radiography apparatus performing tomosynthesis imaging which irradiates an object with radiation emitted from a radiation source at each of a plurality of irradiation positions having different irradiation angles to capture projection images of the object at each of the irradiation positions. The image processing method comprising: acquiring a projection image group including a plurality of projection images obtained by the tomosynthesis imaging in an irradiation angle range wider than an overall imaging irradiation angle range in which a tomographic image including an entire object is obtainable in a case in which the tomographic image is generated using the projection images obtained at each of the plurality of irradiation positions; generating a plurality of first tomographic images including a part of the object, using a plurality of projection images obtained by the tomosynthesis imaging in a first irradiation angle range wider than the overall imaging irradiation angle range among the projection images included in the projection image group; and generating a plurality of second tomographic images including the entire object, using a plurality of projection images obtained by the tomosynthesis imaging in a second irradiation angle range that is equal to or narrower than the overall imaging irradiation angle range among the projection images included in the projection image group.

In addition, in order to achieve the above object, according to a sixteenth aspect of the present disclosure, there is provided an image processing program that is used in a radiography apparatus performing tomosynthesis imaging which irradiates an object with radiation emitted from a radiation source at each of a plurality of irradiation positions having different irradiation angles to capture projection images of the object at each of the irradiation positions. The image processing program causes a computer to perform a process comprising: acquiring a projection image group including a plurality of projection images obtained by the tomosynthesis imaging in an irradiation angle range wider than an overall imaging irradiation angle range in which a tomographic image including an entire object is obtainable in a case in which the tomographic image is generated using the projection images obtained at each of the plurality of irradiation positions; generating a plurality of first tomographic images including a part of the object, using a plurality of projection images obtained by the tomosynthesis imaging in a first irradiation angle range wider than the overall imaging irradiation angle range among the projection images included in the projection image group; and generating a plurality of second tomographic images including the entire object, using a plurality of projection images obtained by the tomosynthesis imaging in a second irradiation angle range that is equal to or narrower than the overall imaging irradiation angle range among the projection images included in the projection image group.

According to the present disclosure, it is possible to generate a high-resolution tomographic image and a tomographic image including the entire object from a projection image group including a plurality of projection images obtained by tomosynthesis imaging in an irradiation angle range in which the entire object is not included in the tomographic image in a case in which the tomographic image is generated using all of the projection images.

BRIEF DESCRIPTION OF THE DRAWINGS

Exemplary embodiments according to the technique of the present disclosure will be described in detail based on the following figures, wherein.

DETAILED DESCRIPTION

Hereinafter, an embodiment of the present disclosure will be described in detail with reference to the drawings. In addition, this embodiment does not limit the present disclosure.

Figure 1:
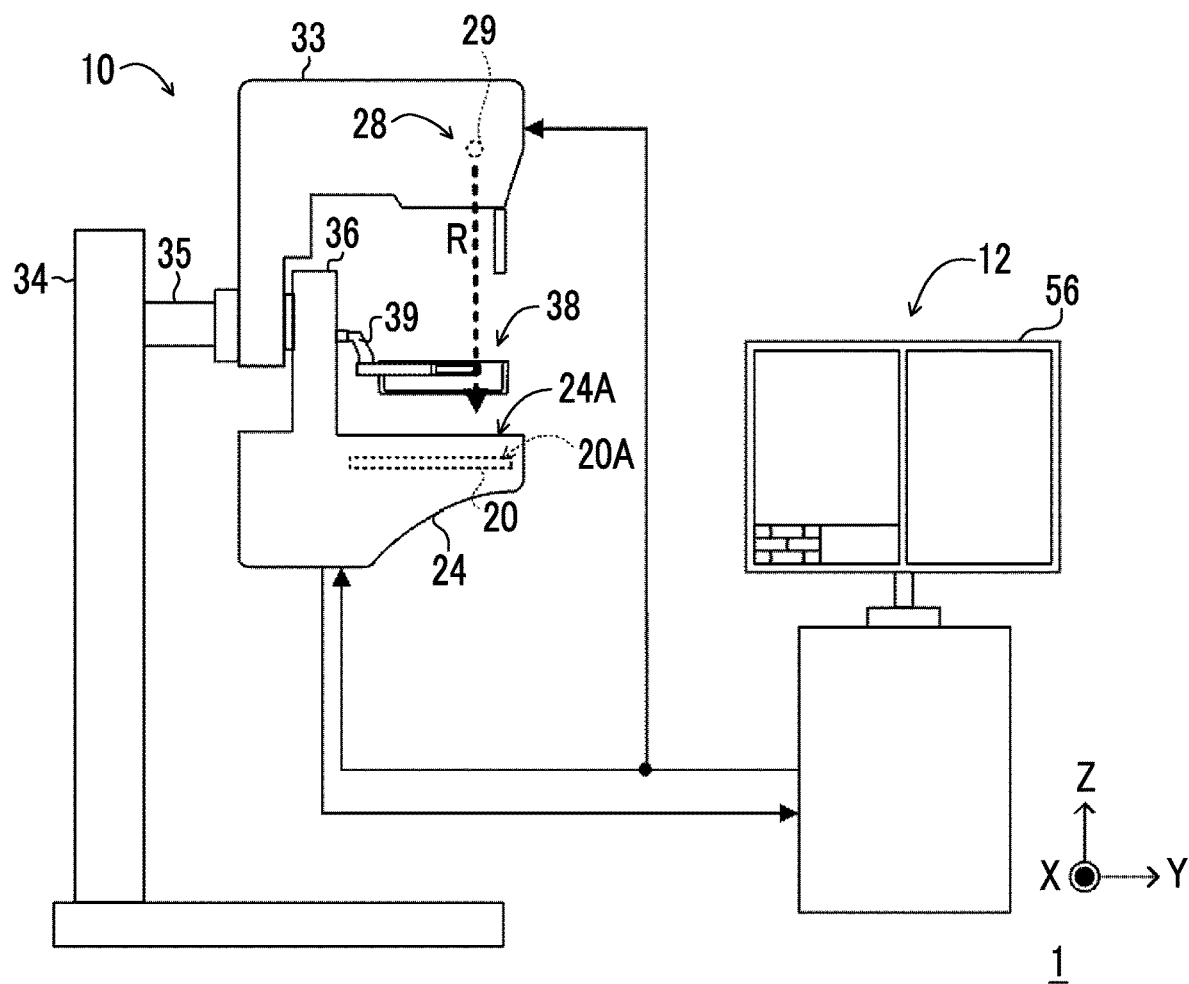
FIG. 1 is a diagram schematically illustrating an example of the overall configuration of a radiography system according to an embodiment.

First, an example of the overall configuration of a radiography system according to this embodiment will be described. FIG. 1 is a diagram illustrating an example of the overall configuration of a radiography system 1 according to this embodiment. As illustrated in FIG. 1, the radiography system 1 according to this embodiment comprises a mammography apparatus 10 and a console 12.

First, the mammography apparatus 10 according to this embodiment will be described. FIG. 1 is a side view illustrating an example of the outward appearance of the mammography apparatus 10 according to this embodiment. In addition, FIG. 1 illustrates an example of the outward appearance of the mammography apparatus 10 as viewed from the left side of a subject.

The mammography apparatus 10 according to this embodiment is an apparatus that is operated under the control of the console 12 and irradiates the breast of the subject as an object with radiation R (for example, X-rays) to capture a radiographic image of the breast. In addition, the mammography apparatus 10 may be an apparatus that images the breast of the subject not only in a state in which the subject is standing (standing state) but also in a state in which the subject is sitting on, for example, a chair (including a wheelchair) (sitting state).

Furthermore, the mammography apparatus 10 according to this embodiment has a function of performing normal imaging that captures images at an irradiation position where a radiation source 29 is disposed along a normal direction to a detection surface 20A of a radiation detector 20 and so-called tomosynthesis imaging that captures images while moving the radiation source 29 to each of a plurality of irradiation positions.

The radiation detector 20 detects the radiation R transmitted through the breast which is the object. Specifically, the radiation detector 20 detects the radiation R that has entered the breast of the subject and an imaging table 24 and reached the detection surface 20A of the radiation detector 20, generates a radiographic image on the basis of the detected radiation R, and outputs image data indicating the generated radiographic image. In the following description, in some cases, a series of operations of emitting the radiation R from the radiation source 29 and generating a radiographic image using the radiation detector 20 is referred to as "imaging". The type of the radiation detector 20 according to this embodiment is not particularly limited. For example, the radiation detector 20 may be an indirect-conversion-type radiation detector that converts the radiation R into light and converts the converted light into charge or a direct-conversion-type radiation detector that directly converts the radiation R into charge.

As illustrated in FIG. 1, the radiation detector 20 is disposed in the imaging table 24. In the mammography apparatus 10 according to this embodiment, in a case in which imaging is performed, the breast of the subject is positioned on an imaging surface 24A of the imaging table 24 by a user.

A compression plate 38 that is used to compress the breast in a case in which imaging is performed is attached to a compression unit 36 that is provided in the imaging table 24. Specifically, the compression unit 36 is provided with a compression plate driving unit (not illustrated) that moves the compression plate 38 in a direction (hereinafter, referred to as an "up-down direction") toward or away from the imaging table 24. A support portion 39 of the compression plate 38 is detachably attached to the compression plate driving unit and is moved in the up-down direction by the compression plate driving unit to compress the breast of the subject between the compression plate 38 and the imaging table 24. The compression plate 38 according to this embodiment is an example of a compression member according to the present disclosure.

As illustrated in FIG. 1, the mammography apparatus 10 according to this embodiment comprises the imaging table 24, an arm portion 33, a base 34, and a shaft portion 35. The arm portion 33 is held by the base 34 so as to be movable in the up-down direction (Z-axis direction). In addition, the arm portion 33 can be rotated with respect to the base 34 by the shaft portion 35. The shaft portion 35 is fixed to the base 34, and the shaft portion 35 and the arm portion 33 are rotated integrally.

Gears are provided in each of the shaft portion 35 and the compression unit 36 of the imaging table 24. The gears can be switched between an engaged state and a non-engaged state to switch between a state in which the compression unit 36 of the imaging table 24 and the shaft portion 35 are connected and rotated integrally and a state in which the shaft portion 35 is separated from the imaging table 24 and runs idle. In addition, components for switching between the transmission and non-transmission of the power of the shaft portion 35 are not limited to the gears, and various mechanical elements may be used.

Each of the arm portion 33 and the imaging table 24 can be relatively rotated with respect to the base 34, using the shaft portion 35 as a rotation axis. In this embodiment, engagement portions (not illustrated) are provided in each of the base 34, the arm portion 33, and the compression unit 36 of the imaging table 24. The state of the engagement portions is switched to connect each of the arm portion 33 and the compression unit 36 of the imaging table 24 to the base 34. One or both of the arm portion 33 and the imaging table 24 connected to the shaft portion 35 are integrally rotated on the shaft portion 35.

Figure 2:
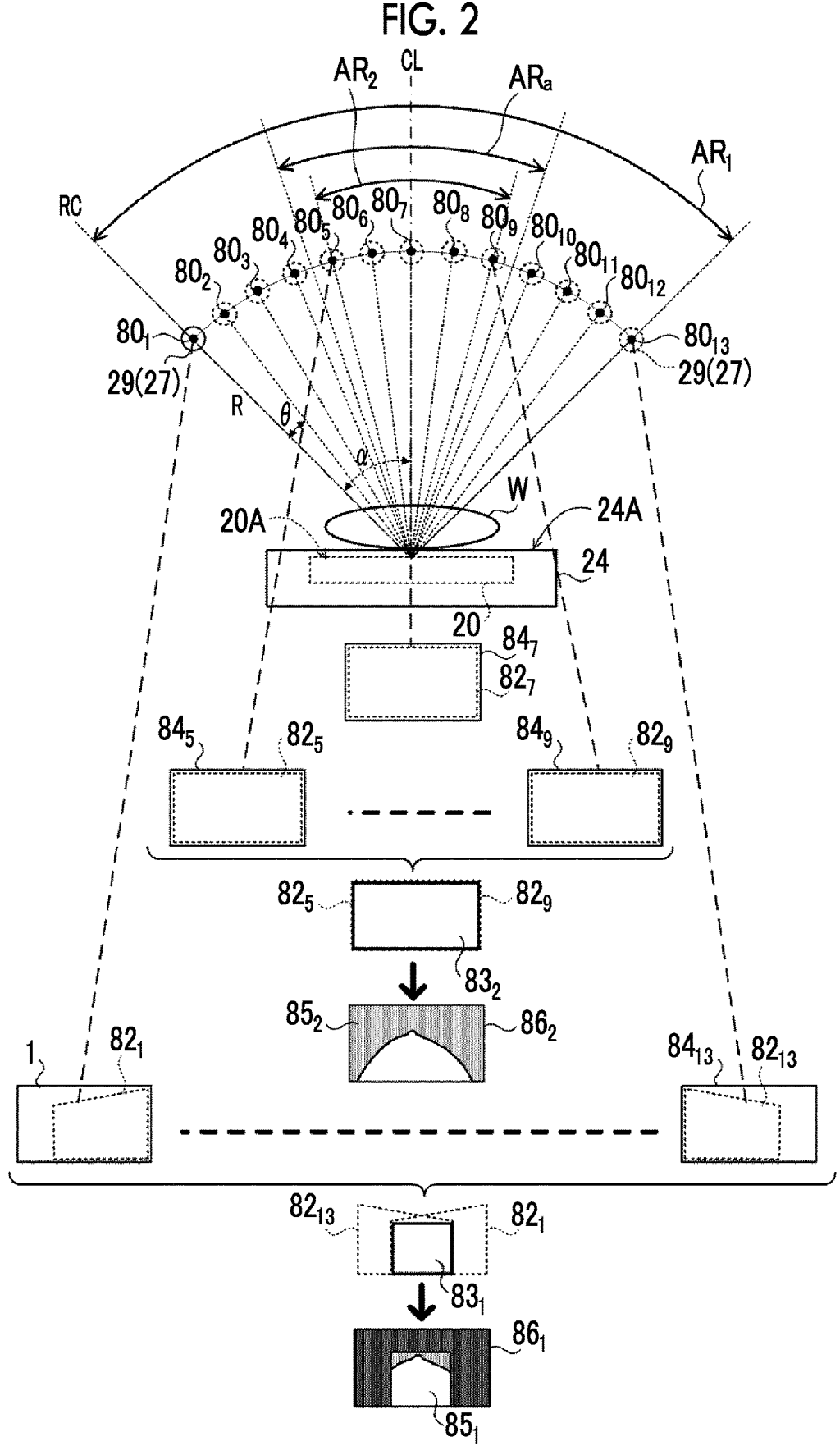
FIG. 2 is a diagram illustrating an example of tomosynthesis imaging.

In a case in which the mammography apparatus 10 performs the tomosynthesis imaging, the radiation source 29 of a radiation emitting unit 28 is sequentially moved to each of a plurality of irradiation positions having different irradiation angles by the rotation of the arm portion 33. The radiation source 29 includes a radiation tube 27 that generates the radiation R, and the radiation tube 27 is moved to each of the plurality of irradiation positions with the movement of the radiation source 29. FIG. 2 is a diagram illustrating an example of the tomosynthesis imaging. In addition, the compression plate 38 is not illustrated in FIG. 2. In this embodiment, as illustrated in FIG. 2, the radiation source 29 is moved to irradiation positions $80_k$ (k=1, 2, . . . ; the maximum value is 13 in FIG. 2) with different irradiation angles which are arranged at an interval of a predetermined angle θ, that is, positions where the radiation R is incident on the detection surface 20A of the radiation detector 20 at different angles. At each of the irradiation positions $80_k$, the radiation source 29 emits the radiation R to a breast W in response to an instruction from the console 12, and the radiation detector 20 captures a radiographic image. In the radiography system 1, in a case in which the tomosynthesis imaging that moves the radiation source 29 to each of the irradiation positions $80_k$ and captures radiographic images at each of the irradiation positions $80_k$ is performed, 13 radiographic images are obtained in the example illustrated in FIG. 2. In addition, in the following description, in the tomosynthesis imaging, in a case in which a radiographic image captured at each irradiation position 80 is distinguished from other radiographic images, it is referred to as a "projection image". Further, in a case in which a radiographic image is generically referred to regardless of the type, such as a projection image and a tomographic image which will be described below, it is simply referred to as a "radiographic image". Furthermore, in the following description, in a case in which the irradiation positions $80_k$ are generically referred to, a reference letter k for distinguishing each irradiation position is omitted, and the irradiation positions $80_k$ are referred to as "irradiation positions 80".

In addition, as illustrated in FIG. 2, the incident angle of the radiation R means an angle α formed between a normal line CL to the detection surface 20A of the radiation detector 20 and a radiation axis RC. The radiation axis RC means an axis that connects the focus of the radiation tube 27 of the radiation source 29 at each irradiation position 80 and a preset position such as the center of the detection surface 20A. Further, here, it is assumed that the detection surface 20A of the radiation detector 20 is substantially parallel to the imaging surface 24A. Hereinafter, a predetermined range in which the incident angles are different in the tomosynthesis imaging as illustrated in FIG. 2 is referred to as an "irradiation angle range". Furthermore, in this embodiment, the "incident angle" and the "irradiation angle" of the radiation R are synonymous.

Further, FIG. 2 illustrates object regions $82_1$, $82_5$, $82_7$, $82_9$, $82_{13}$ which are included in projection images $84_1$, $84_5$, $84_7$, $84_9$, and $84_{13}$ obtained in a case in which the radiation source 29 is located at the irradiation positions $80_1$, $80_5$, $80_7$, $80_9$, and $80_{13}$, respectively. The object region 82 corresponds to the irradiation field of the radiation R on the detection surface 20A of the radiation detector 20. In this embodiment, in a case in which the object regions 82, the projection images 84, and the tomographic images 86 have a correspondence relationship with the irradiation positions 80, numbers "1 to 13" indicating the irradiation positions $80_1$ to $80_{13}$, respectively, are added to the reference numerals. For example, in a case in which the radiation source 29 is located at the seventh irradiation position $80_7$, the projection image $84_7$ including the object region $82_7$ is obtained. Further, in the following description, for simplicity, the projection image 84 obtained in a case in which the radiation source 29 is located at a certain irradiation position 80 is simply referred to as a "projection image 84 obtained at the irradiation position 80".

The object region $82_7$ which is included in the projection image $84_7$ obtained at the seventh irradiation position $80_7$ along the normal line CL where the irradiation angle is 0 degrees has the range and size in which the entire image of the breast W, which is the object, can be captured.

As the angle α becomes larger, in other words, as the incident angle of the radiation R obliquely incident on the detection surface 20A of the radiation detector 20 becomes larger, the influence of the oblique incidence of the radiation R becomes larger, and the radiation field of the radiation R becomes narrower. Therefore, as illustrated in FIG. 2, as the angle α becomes larger, the object region 82 included in the projection image 84 becomes narrower. In other words, in a case in which the radiation source 29 is located at the irradiation position 80 having a relatively large irradiation angle, the influence of the oblique incidence of the radiation R becomes large. Therefore, the object region 82 included in the obtained projection image 84 is narrower than the object region $82_7$. In the example illustrated in FIG. 2, both the object region $82_1$ included in the projection image $84_1$ obtained at the irradiation position $80_1$ having the largest irradiation angle and the object region $82_{13}$ included in the projection image $84_{13}$ obtained at the irradiation position $80_{13}$ are narrower than the object region $82_7$. Specifically, the object region $82_1$ and the object region $82_{13}$ have a shape in which a region on the side where the radiation source 29 is located during imaging has missed. As described above, for example, the size of the object region 82 included in the projection image 84 varies depending on the irradiation position 80.

In a case in which a tomographic image 86 is reconstructed using a plurality of projection images 84 obtained by the tomosynthesis imaging, a reconstructed region depends on the object region 82 in each projection image 84. Specifically, the reconstructed region is limited to a common partial region (hereinafter, referred to as a "partial region") of the object regions 82 included in all of the projection images 84 used to generate the tomographic image 86.

As illustrated in FIG. 2, in the case of the irradiation position 80 where the irradiation angle is relatively small, even though the radiation R emitted from the radiation source 29 is obliquely incident on the detection surface 20A of the radiation detector 20, the object region 82 having the same shape and size as the object region $82_7$ is obtained. In a case in which the object region 82 included in the projection image 84 obtained at each of the plurality of irradiation positions 80 is equivalent to the object region $82_7$, a partial region 83, that is, a reconstructed region 85 is also equivalent to the object region $82_7$. In this case, since the entire object region 82 included in each projection image 84 is regarded as the partial region 83, it cannot be said to be a "part" in a strict sense, but is referred to as a "part" for convenience of explanation. In a case in which the reconstructed region 85 is equivalent to the object region $82_7$, the tomographic image 86 is an image in which the entire object is included. Further, the "entire object" included in the tomographic image 86 means, for example, a portion captured by the radiation detector 20 in a case in which radiation is emitted at the irradiation position where the irradiation angle α is 0 degrees in the object to be imaged such as the breast. Furthermore, the entire object is about a plane in which the radiation R is projected onto the object. The entire object does not mean, for example, the entire breast, but means at least the entire region of the object desired by the user for interpretation. For example, the entire object also includes a region in which an end portion of the object that is not required for interpretation or the like has missed.

As described above, the irradiation angle range, which is the range of the irradiation positions 80 where the projection images 84 that can make the reconstructed region 85 in the tomographic image 86 equivalent to the object region $82_7$ are obtained, is referred to as an overall imaging irradiation angle range $AR_a$ (See FIG. 2). That is, the overall imaging irradiation angle range $AR_a$ means an irradiation angle range in which the tomographic image 86 including the entire object can be obtained in a case in which the tomographic image 86 is generated using the projection images 84 obtained at each of the plurality of irradiation positions 80. Strictly speaking, the overall imaging irradiation angle range $AR_a$ means the maximum irradiation angle range in which the tomographic image 86 including the entire object can be obtained.

In a case in which the irradiation angle range is wider than the overall imaging irradiation angle range $AR_a$, the reconstructed region 85 in the tomographic image 86 is narrower than the object region $82_7$. Therefore, the tomographic image 86 is an image including a part of the object.

In FIG. 2, a first irradiation angle range $AR_1$ is illustrated as an irradiation angle range wider than the overall imaging irradiation angle range $AR_a$. In a case in which the irradiation angle range is the first irradiation angle range $AR_1$, a partial region $83_1$ common to the object regions $82_1$ to $82_{13}$ included in the projection images $84_1$ to $84_{13}$ obtained at each of the irradiation positions $80_1$ to $80_{13}$ corresponds to a reconstructed region $85_1$ in a case in which a first tomographic image $86_1$ is generated. The partial region $83_1$, that is, the reconstructed region $85_1$ is smaller than the object regions $82_1$ to $82_{13}$ included in the projection images $84_1$ to $84_{13}$.

In the first tomographic image $86_1$, the reconstructed region $85_1$ is a region in which the object can be included. Therefore, the first tomographic image $86_1$ is an image in which a part of the object is included. For example, FIG. 2 illustrates the first tomographic image $86_1$ in which a part of the breast W, which is the object, is included.

The resolution of the tomographic image 86 depends on the irradiation angle range. As the irradiation angle range becomes wider, the resolution of the tomographic image 86 becomes higher. Therefore, the first tomographic image $86_1$ generated by the plurality of projection images $84_1$ to $84_{13}$ obtained by the tomosynthesis imaging in the first irradiation angle range $AR_1$ is a high-resolution image.

On the other hand, in a case in which the irradiation angle range is equal to or narrower than the overall imaging irradiation angle range $AR_a$, the reconstructed region 85 in the tomographic image 86 is equivalent to the object region $82_7$. Therefore, the tomographic image 86 is an image in which the entire object is included.

In FIG. 2, a second irradiation angle range $AR_2$ is illustrated as an irradiation angle range that is equal to or narrower than the overall imaging irradiation angle range $AR_a$. In a case in which the irradiation angle range is the second irradiation angle range $AR_2$, a partial region $83_2$ common to the object regions $82_5$ to $82_9$ included in the projection images $84_5$ to $84_9$ obtained at each of the irradiation positions $80_5$ to $80_9$ corresponds to the reconstructed region $85_2$ in a case in which a second tomographic image $86_2$ is generated. The partial region $83_2$, that is, the reconstructed region $85_2$ is equivalent to the object regions $82_5$ to $82_9$ included in the projection images $84_5$ to $84_9$.

In the second tomographic image $86_2$, the reconstructed region $85_2$ is a region in which the object can be included. Therefore, the second tomographic image $86_2$ is an image in which the entire object is included. For example, FIG. 2 illustrates the second tomographic image $86_2$ in which the entire breast W which is the object is included.

The resolution of the tomographic image 86 depends on the irradiation angle range. As the irradiation angle range becomes narrower, the resolution of the tomographic image 86 becomes lower. Therefore, the second tomographic image $86_2$ generated by the plurality of projection images $84_5$ to $84_9$ obtained by the tomosynthesis imaging in the second irradiation angle range $AR_2$ has a lower resolution than the first tomographic image $86_1$.

As described above, in a case in which the irradiation angle range is equal to or narrower than the overall imaging irradiation angle range $AR_a$, the tomographic image 86 generated by the projection images 84 obtained at each irradiation position 80 is a tomographic image in which the entire object is included. In a case in which the irradiation angle range is wider than the overall imaging irradiation angle range $AR_a$, the tomographic image 86 generated by the projection images 84 obtained at each irradiation position 80 is a tomographic image which includes a part of the object, but has a high resolution.

Figure 3:
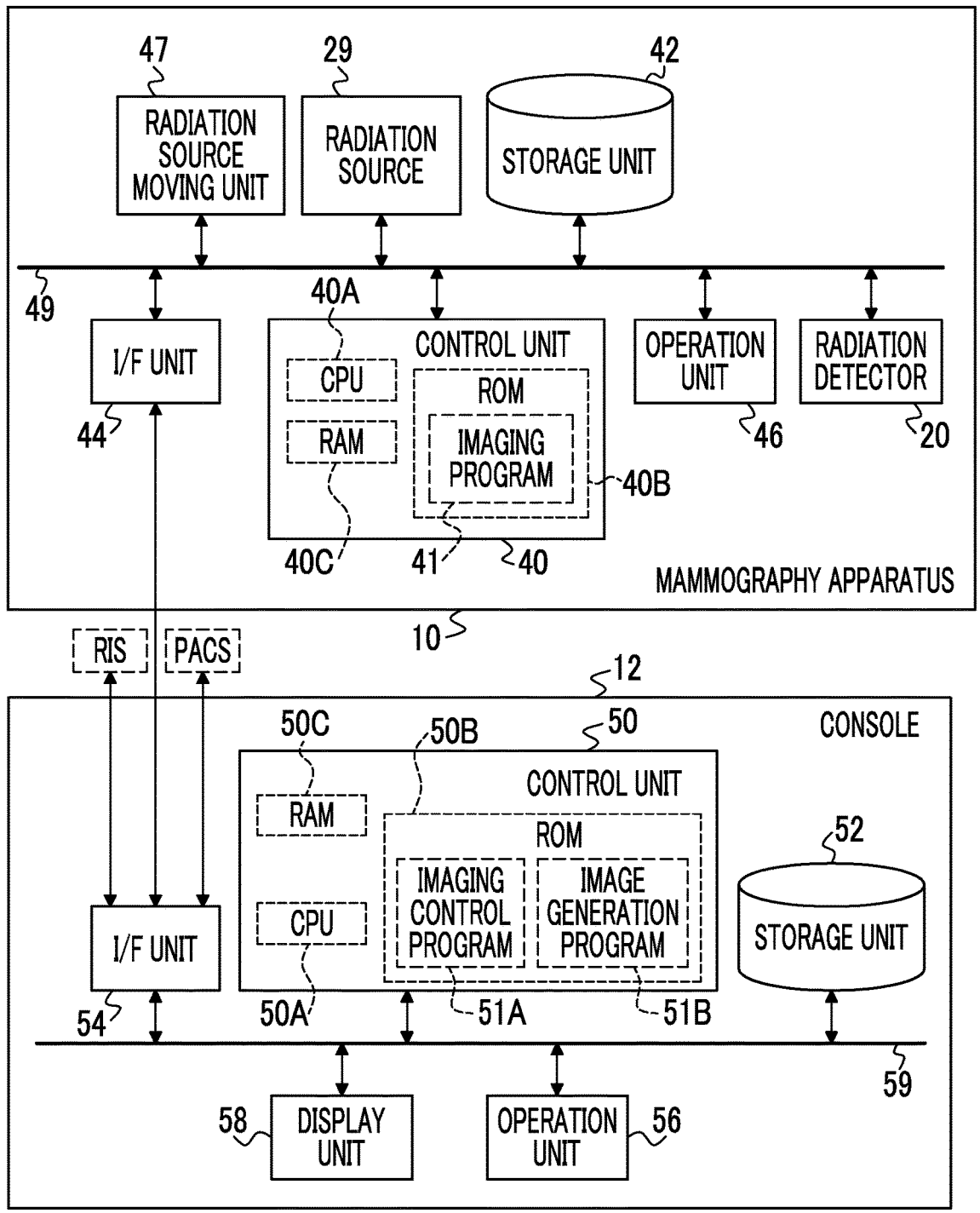
FIG. 3 is a block diagram illustrating an example of the configuration of a mammography apparatus and a console according to the embodiment.

Further, FIG. 3 is a block diagram illustrating an example of the configuration of the mammography apparatus 10 and the console 12 according to the embodiment. As illustrated in FIG. 3, the mammography apparatus 10 according to this embodiment further comprises a control unit 40, a storage unit 42, an interface (I/F) unit 44, an operation unit 46, and a radiation source moving unit 47. The control unit 40, the storage unit 42, the I/F unit 44, the operation unit 46, and the radiation source moving unit 47 are connected to each other through a bus 49, such as a system bus or a control bus, such that they can transmit and receive various kinds of information.

The control unit 40 controls the overall operation of the mammography apparatus 10 under the control of the console 12. The control unit 40 comprises a central processing unit (CPU) 40A, a read only memory (ROM) 40B, and a random access memory (RAM) 40C. For example, various programs including an imaging program 41 which is executed by the CPU 40A and performs control related to the capture of a radiographic image are stored in the ROM 40B in advance. The RAM 40C temporarily stores various kinds of data.

For example, the image data of the radiographic image captured by the radiation detector 20 and various other kinds of information are stored in the storage unit 42. A specific example of the storage unit 42 is a hard disk drive (HDD), a solid state drive (SSD), or the like. The I/F unit 44 transmits and receives various kinds of information to and from the console 12 using wireless communication or wired communication. The image data of the radiographic image captured by the radiation detector 20 in the mammography apparatus 10 is transmitted to the console 12 through the I/F unit 44 by wireless communication or wired communication.

Each of the control unit 40, the storage unit 42, and the I/F unit 44 according to this embodiment is provided in the imaging table 24.

In addition, the operation unit 46 is provided as a plurality of switches in, for example, the imaging table 24 of the mammography apparatus 10. Further, the operation unit 46 may be provided as a touch panel switch or may be provided as a foot switch that is operated by the feet of the user such as a doctor or a radiology technician.

The radiation source moving unit 47 has a function of moving the radiation source 29 to each of the plurality of irradiation positions 80 under the control of the control unit 40 in a case in which the tomosynthesis imaging is performed as described above. Specifically, the radiation source moving unit 47 rotates the arm portion 33 with respect to the imaging table 24 to move the radiation source 29 to each of the plurality of irradiation positions 80. The radiation source moving unit 47 according to this embodiment is provided inside the arm portion 33.

On the other hand, the console 12 according to this embodiment has a function of controlling the mammography apparatus 10 using, for example, an imaging order and various kinds of information acquired from a radiology information system (RIS) through a wireless communication local area network (LAN) and instructions input by the user through an operation unit 56 or the like.

For example, the console 12 according to this embodiment is a server computer. As illustrated in FIG. 3, the console 12 comprises a control unit 50, a storage unit 52, an I/F unit 54, the operation unit 56, and a display unit 58. The control unit 50, the storage unit 52, the I/F unit 54, the operation unit 56, and the display unit 58 are connected to each other through a bus 59, such as a system bus or a control bus, such that they can transmit and receive various kinds of information.

The control unit 50 according to this embodiment controls the overall operation of the console 12. The control unit 50 comprises a CPU 50A, a ROM 50B, and a RAM 50C. Various programs including an imaging control program 51A and an image generation program 51B executed by the CPU 50A are stored in the ROM 50B in advance. The RAM 50C temporarily stores various kinds of data. In this embodiment, the CPU 50A is an example of a processor according to the present disclosure, and the console 12 is an example of an image processing device and an imaging control device according to the present disclosure. In addition, the image generation program 51B according to this embodiment is an example of an image processing program according to the present disclosure.

For example, the image data of the radiographic image captured by the mammography apparatus 10 and various other kinds of information are stored in the storage unit 52. A specific example of the storage unit 52 is an HDD, an SSD, or the like.

The operation unit 56 is used by the user to input instructions, which are related to, for example, the capture of a radiographic image and include an instruction to emit the radiation R, various kinds of information, and the like. The operation unit 56 is not particularly limited. Examples of the operation unit 56 include various switches, a touch panel, a touch pen, and a mouse. The display unit 58 displays various kinds of information. In addition, the operation unit 56 and the display unit 58 may be integrated into a touch panel display.

The I/F unit 54 transmits and receives various kinds of information to and from the mammography apparatus 10, the RIS, and a picture archiving and communication system (PACS) using wireless communication or wired communication. In the radiography system 1 according to this embodiment, the console 12 receives the image data of the radiographic image captured by the mammography apparatus 10 from the mammography apparatus 10 through the I/F unit 54, using wireless communication or wired communication.

Figure 4:
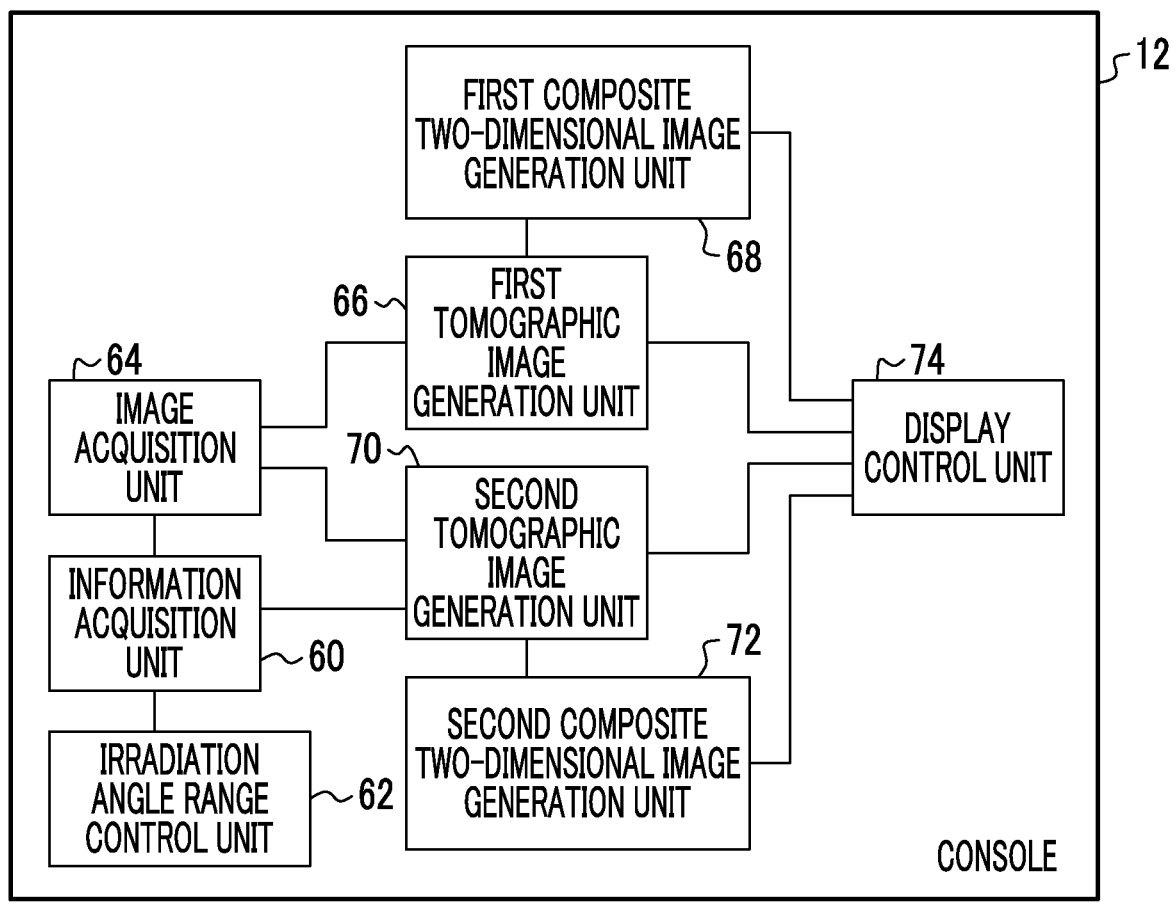
FIG. 4 is a functional block diagram illustrating an example of the functions of the console according to the embodiment.

The console 12 according to this embodiment has a function of controlling the irradiation angle range in the tomosynthesis imaging. Further, the console 12 according to this embodiment has a function of generating a tomographic image from the projection images obtained by the tomosynthesis imaging. FIG. 4 is a functional block diagram illustrating an example of the configuration of the console 12 according to this embodiment related to the function of controlling the irradiation angle range and the function of generating a tomographic image. As illustrated in FIG. 4, the console 12 comprises an information acquisition unit 60, an irradiation angle range control unit 62, an image acquisition unit 64, a first tomographic image generation unit 66, a first composite two-dimensional image generation unit 68, a second tomographic image generation unit 70, a second composite two-dimensional image generation unit 72, and a display control unit 74. For example, in the console 12 according to this embodiment, the CPU 50A of the control unit 50 executes the imaging control program 51A stored in the ROM 50B to function as the information acquisition unit 60 and the irradiation angle range control unit 62. Further, in the console 12, the CPU 50A of the control unit 50 executes the image generation program 51B stored in the ROM 50B to function as the information acquisition unit 60, the image acquisition unit 64, the first tomographic image generation unit 66, the first composite two-dimensional image generation unit 68, the second tomographic image generation unit 70, the second composite two-dimensional image generation unit 72, and the display control unit 74.

The information acquisition unit 60 has a function of acquiring overall imaging information indicating the overall imaging irradiation angle range $AR_a$. As described above, the overall imaging irradiation angle range $AR_a$ is the irradiation angle range in which the projection images 84 capable of generating the tomographic image 86 including the entire object can be obtained. The overall imaging irradiation angle range $AR_a$ depends on the thickness of the object and the area of the object. The "thickness of the object" means the thickness of the breast compressed by the compression plate 38. In this embodiment, the "thickness of the object" means the distance from the imaging surface 24A of the imaging table 24 to a compression surface of the compression plate 38 which compresses the breast.

Figure 5:
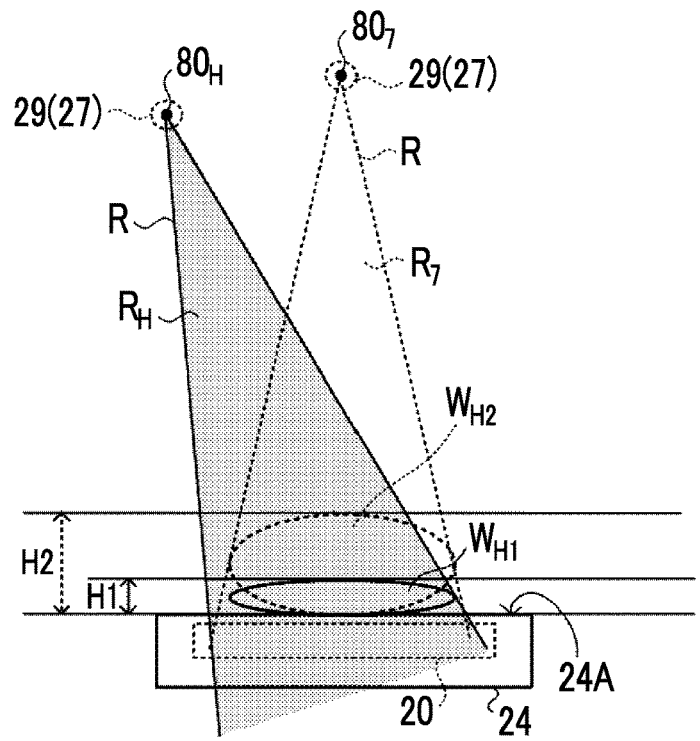
FIG. 5 is a diagram illustrating a relationship between an irradiation angle range and the thickness of an object.

In the example illustrated in FIG. 5, in a case in which the radiation source 29 is located at the irradiation position $80_7$, both the entire breast $W_{H1}$ having a thickness H1 and the entire breast $W_{H2}$ having a thickness H2 larger than the thickness H1 are present in a region $R_7$ to which the radiation R is emitted. Therefore, the projection image 84 obtained at the irradiation position $80_7$ includes both the entire breast $W_{H1}$ and the entire breast $W_{H2}$.

On the other hand, in a case in which the radiation source 29 is located at an irradiation position $80_H$, the entire breast $W_{H1}$ is present in a region $R_H$ in which the radiation R is emitted. On the other hand, the breast $W_{H2}$ does not fall within the region $R_H$ in which the radiation R is emitted and is present outside the region $R_H$. Therefore, the projection image 84 obtained at the irradiation position $80_H$ includes the entire breast $W_{H1}$ and a part of the breast $W_{H2}$.

As described above, as the thickness of the object becomes larger, the irradiation angle of the radiation R capable of capturing an image including the entire object becomes smaller. Therefore, in a case in which the thickness of the object is large, the overall imaging irradiation angle range $AR_a$ is narrow.

In addition, the "area of the object" means the area of the breast that is compressed by the compression plate 38 and is irradiated with the radiation R. In this embodiment, the "area of the object" means the contact area of the breast with the imaging surface 24A of the imaging table 24 or the contact area of the breast with the compression plate 38.

Figure 6:
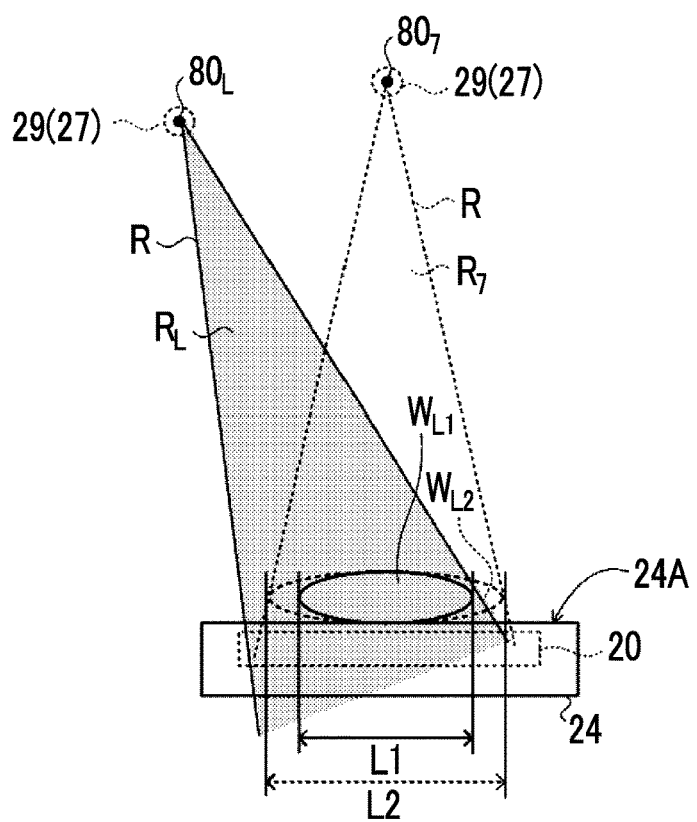
FIG. 6 is a diagram illustrating a relationship between the irradiation angle range and the area of the object.

As the area of the breast becomes larger, the width of the breast becomes larger. Therefore, in the example illustrated in FIG. 6, the area of a breast $W_{L2}$ having a width L2 is larger than that of a breast $W_{L1}$ having a width L1. In a case in which the radiation source 29 is located at the irradiation position $80_7$, both the entire breast $W_{L1}$ having the width L1 and the entire breast $W_{L2}$ having the width L2 larger than the width L1 are present in the region $R_7$ in which the radiation R is emitted. Therefore, the projection image 84 obtained at the irradiation position $80_7$ includes both the entire breast $W_{L1}$ and the entire breast $W_{L2}$. However, in a case in which the radiation source 29 is located at an irradiation position $80_L$, the entire breast $W_{L1}$ is present in a region $R_L$ in which the radiation R is emitted. On the other hand, the breast $W_2$ does not fall within the region $R_L$ in which the radiation R is emitted and is present outside the region $R_L$. Therefore, the projection image 84 obtained at the irradiation position $80_L$ includes the entire breast $W_{L1}$ and a part of the breast $W_{L2}$.

As described above, as the area of the object becomes larger, the irradiation angle of the radiation R capable of capturing an image including the entire object becomes smaller. Therefore, in a case in which the area of the object is large, the overall imaging irradiation angle range $AR_a$ is narrow.

As described above, since the overall imaging irradiation angle range $AR_a$ changes depending on the thickness of the breast and the area of the breast, the information acquisition unit 60 according to this embodiment acquires the overall imaging information indicating the overall imaging irradiation angle range $AR_a$.

For example, in this embodiment, irradiation angle range correspondence relationship information in which the thickness of the breast and the area of the breast are associated with the overall imaging irradiation angle range $AR_a$ is obtained in advance. The information acquisition unit 60 acquires the overall imaging information indicating the overall imaging irradiation angle range $AR_a$ with reference to the irradiation angle range correspondence relationship information.

First, the information acquisition unit 60 acquires the thickness and area of the breast compressed by the compression plate 38. A method by which the information acquisition unit 60 acquires the thickness of the breast is not particularly limited. For example, in this embodiment, the information acquisition unit 60 acquires the thickness of the breast on the basis of the amount of movement of the compression plate 38 by the compression unit 36 in a case in which the breast is compressed.

Further, a method by which the information acquisition unit 60 acquires the area of the breast is not particularly limited. For example, in this embodiment, the information acquisition unit 60 acquires the area of the breast on the basis of the size of the breast input by the user through the operation unit 56 of the console 12. Specifically, area correspondence relationship information in which information indicating the size of the breast, such as a large size, a medium size, and a small size, and the average area of the breast at the size are associated with each other is obtained in advance. The information acquisition unit 60 acquires the area of the breast corresponding to the size of the breast input by the user through the operation unit 56 with reference to the area correspondence relationship information.

A method by which the information acquisition unit 60 acquires the area of the breast is not limited to this aspect. For example, a contact sensor may be provided in the surface of the imaging table 24 or the compression plate 38 which comes into contact with the breast, and the information acquisition unit 60 may acquire the area of the breast according to the range in which the contact sensor detects the contact of the breast. In addition, for example, a visible light imaging device that captures an image with visible light may be used, and the information acquisition unit 60 may acquire a visible light image of a compressed surface of the breast compressed by the compression plate 38 and acquire the area of the breast according to the size of a breast region included in the visible light image.

In addition, the information acquisition unit 60 acquires the overall imaging information indicating the overall imaging irradiation angle range $AR_a$ which corresponds to the thickness and area of the breast with reference to the irradiation angle range correspondence relationship information. Then, the information acquisition unit 60 outputs the acquired overall imaging information to the irradiation angle range control unit 62, the image acquisition unit 64, and the second tomographic image generation unit 70.

The irradiation angle range control unit 62 has a function of directing the mammography apparatus 10 to execute control to perform the tomosynthesis imaging in an irradiation angle range which is wider than the overall imaging irradiation angle range $AR_a$ corresponding to the overall imaging information. The irradiation angle range control unit 62 according to this embodiment sets, as the irradiation angle range, the first irradiation angle range $AR_1$ wider than the overall imaging irradiation angle range $AR_a$ corresponding to the overall imaging information input from the information acquisition unit 60 for the mammography apparatus 10. In the mammography apparatus 10, the control unit 40 directs the radiation source moving unit 47 to move the radiation source 29 and performs the tomosynthesis imaging in the irradiation angle range set by the console 12. Therefore, the mammography apparatus 10 performs the tomosynthesis imaging in the first irradiation angle range $AR_1$ as the irradiation angle range. In addition, the extent to which the irradiation angle range control unit 62 makes the first irradiation angle range $AR_1$ wider than the overall imaging irradiation angle range $AR_a$ is not particularly limited. That is, a difference between the first irradiation angle range $AR_1$ and the overall imaging irradiation angle range $AR_a$ is not particularly limited. For example, the difference between the first irradiation angle range $AR_1$ and the overall imaging irradiation angle range $AR_a$ may be a predetermined value, such as ±15 degrees, or a value corresponding to the desired resolution.

The image acquisition unit 64 has a function of acquiring a projection image group including a plurality of projection images 84 obtained by the tomosynthesis imaging in an irradiation angle range wider than the overall imaging irradiation angle range $AR_a$. Specifically, the image acquisition unit 64 according to this embodiment acquires the projection images $84_1$ to $84_{13}$ obtained by the tomosynthesis imaging in the first irradiation angle range $AR_1$ as the irradiation angle range wider than the overall imaging irradiation angle range $AR_a$ corresponding to the overall imaging information input from the information acquisition unit 60. The image acquisition unit 64 outputs image data indicating the acquired projection images $84_1$ to $84_{13}$ to the first tomographic image generation unit 66 and the second tomographic image generation unit 70.

The first tomographic image generation unit 66 has a function of generating a plurality of first tomographic images $86_1$ including a part of the object, using a plurality of projection images $84_1$ to $84_{13}$ obtained by the tomosynthesis imaging in the first irradiation angle range $AR_1$ among the projection images included in the projection image group acquired by the image acquisition unit 64. A method by which the first tomographic image generation unit 66 generates the plurality of first tomographic images $86_1$ is not particularly limited, and a known method may be used. For example, reconstruction may be performed by a back projection method, such as a filter back projection (FBP) method or an iterative reconstruction method, or a known technique may be applied. The slice thickness (hereinafter, referred to as a "first slice thickness") of the tomographic images $86_1$ generated by the first tomographic image generation unit 66 is not particularly limited. In addition, as the resolution of the tomographic image becomes higher, the slice thickness can become smaller. Therefore, in this embodiment, the first slice thickness is smaller than the slice thickness of the second tomographic image $86_2$ (hereinafter, referred to as a "second slice thickness"). Specifically, the first slice thickness can be determined according to, for example, the size of a region of interest, the quality of the radiographic image, the processing load of arithmetic processing in the generation, and an instruction from the user. The first tomographic image generation unit 66 outputs image data indicating the generated plurality of first tomographic images $86_1$ to the first composite two-dimensional image generation unit 68 and the display control unit 74.

The first composite two-dimensional image generation unit 68 has a function of generating a first composite two-dimensional image obtained by combining at least some of the plurality of first tomographic images $86_1$. The first composite two-dimensional image generation unit 68 outputs image data indicating the generated first composite two-dimensional image to the display control unit 74.

A method by which the first composite two-dimensional image generation unit 68 generates the first composite two-dimensional image is not particularly limited, and a known method may be used. For example, the first composite two-dimensional image generation unit 68 uses the method described in the specification of U.S. Pat. No. 8,983,156B. U.S. Pat. No. 8,983,156B discloses a technique that blends (combines) a region of interest (ROI) detected from a tomographic image with a two-dimensional image to a composite two-dimensional image in which a lesion or the like detected from the tomographic image has been reflected. In addition, a method for detecting the region of interest from the tomographic image is not particularly limited. For example, a method that extracts the region of interest from the tomographic image using a known computer-aided diagnosis (hereinafter, referred to as CAD) algorithm is given as an example. In the CAD algorithm, preferably, the probability (for example, likelihood) that a pixel in the tomographic image will be the region of interest is derived, and the pixel is detected as a pixel constituting the image of the region of interest in a case in which the probability is equal to or greater than a predetermined threshold value. Further, for example, a method may be used which extracts the region of interest from the tomographic image by a filtering process or the like using a filter for extracting the region of interest.

Further, as a method by which the first composite two-dimensional image generation unit 68 generates the first composite two-dimensional image, for example, a method may be used which generates a composite two-dimensional image by projecting a plurality of tomographic images, or at least one of the plurality of tomographic images and at least one of a plurality of projection images in a depth direction in which the tomographic planes of the breast are arranged or by using a minimum intensity projection method, which is disclosed in JP2014-128716A. In addition, for example, a method may be used which generates a composite two-dimensional image by reconstructing a plurality of tomographic images or at least one of the plurality of tomographic images and at least one of a plurality of projection images using any one of a filtered back projection method, a maximum likelihood reconstruction method, an iterative reconstruction method, a reconstruction method using an algebraic method, or a three-dimensional reconstruction method, which is disclosed in JP6208731B.

On the other hand, the second tomographic image generation unit 70 has a function of generating a plurality of second tomographic images $86_2$ including the entire object, using a plurality of projection images $84_5$ to $84_9$ obtained by the tomosynthesis imaging in the second irradiation angle range $AR_2$ among the projection images included in the projection image group acquired by the image acquisition unit 64. Specifically, the second tomographic image generation unit 70 acquires the projection images $84_5$ to $84_9$ obtained by the tomosynthesis imaging in the second irradiation angle range $AR_2$ which is an irradiation angle range equal to or narrower than the overall imaging irradiation angle range $AR_a$ corresponding to the overall imaging information input from the information acquisition unit 60 from the image acquisition unit 64. Then, the second tomographic image generation unit 70 generates a plurality of second tomographic images $86_2$ using the acquired projection images $84_5$ to $84_9$. The second slice thickness of the second tomographic image $86_2$ is not particularly limited. However, in this embodiment, as described above, the second slice thickness is larger than the first slice thickness. Specifically, the second slice thickness can be determined according to, for example, the size of the region of interest, the quality of the radiographic image, the processing load of arithmetic processing in the generation, and an instruction from the user. In addition, a method by which the second tomographic image generation unit 70 generates the plurality of second tomographic images $86_2$ is not particularly limited. For example, the same method as that by which the first tomographic image generation unit 66 generates the first tomographic image $86_1$ may be applied. The second tomographic image generation unit 70 outputs image data indicating the generated plurality of second tomographic images $86_2$ to the second composite two-dimensional image generation unit 72 and the display control unit 74.

The second composite two-dimensional image generation unit 72 has a function of generating a second composite two-dimensional image obtained by combining at least some of the plurality of second tomographic images $86_2$. The second composite two-dimensional image generation unit 72 outputs image data indicating the generated second composite two-dimensional image to the display control unit 74. A method by the second composite two-dimensional image generation unit 72 generates the second composite two-dimensional image is not particularly limited. For example, the same method as that by which the first composite two-dimensional image generation unit 68 generates the first composite two-dimensional image may be applied.

The display control unit 74 has a function of displaying at least one of the first tomographic image $86_1$, the second tomographic image $86_2$, the first composite two-dimensional image, or the second composite two-dimensional image on the display unit 58. The display form of these images by the display control unit 74 will be described in detail below.

Next, the operation of the console 12 in the tomosynthesis imaging will be described with reference to the drawings. After directing the mammography apparatus 10 to perform the tomosynthesis imaging (FIG. 7, Step S10), the console 12 generates various radiographic images using the projection image group obtained by the tomosynthesis imaging and displays the radiographic images on, for example, the display unit 58 (See FIG. 7, Step S12).

First, the operation of the console 12 directing the mammography apparatus 10 to perform the tomosynthesis imaging in Step S10 of FIG. 7 will be described. In a case in which the tomosynthesis imaging is performed, the user positions the breast as the object on the imaging table 24 of the mammography apparatus 10 and compresses the breast with the compression plate 38. In a case in which the compression of the breast is completed, the console 12 performs an imaging control process illustrated in FIG. 8. Specifically, in a case in which the console 12 receives information indicating that the compression of the breast has been completed in a state in which an instruction to perform the tomosynthesis imaging is included in the imaging menu acquired from RIS, the console 12 performs the imaging control process illustrated in FIG. 8. FIG. 8 is a flowchart illustrating an example of the flow of the imaging control process performed by the console 12 according to this embodiment. In the console 12 according to this embodiment, for example, the CPU 50A of the control unit 50 executes the imaging control program 51A stored in the ROM 50B to perform the imaging control process whose example is illustrated in FIG. 8.

In Step S100 of FIG. 8, the information acquisition unit 60 acquires the thickness of the breast. As described above, the information acquisition unit 60 according to this embodiment acquires the thickness of the breast on the basis of the amount of movement of the compression plate 38 by the compression unit 36 in a case in which the breast is compressed.

Then, in Step S102, the information acquisition unit 60 acquires the area of the breast. As described above, the information acquisition unit 60 according to this embodiment acquires the area of the breast on the basis of the size of the breast input by the user through the operation unit 56 of the console 12.

Then, in Step S104, the information acquisition unit 60 acquires the overall imaging information indicating the overall imaging irradiation angle range $AR_a$. As described above, the information acquisition unit 60 according to this embodiment acquires the overall imaging information corresponding to the thickness of the breast acquired in Step S100 and the area of the breast acquired in Step S102 with reference to the irradiation angle range correspondence relationship information.

Then, in Step S106, the irradiation angle range control unit 62 sets the irradiation angle range in the tomosynthesis imaging for the mammography apparatus 10. As described above, the irradiation angle range control unit 62 according to this embodiment specifies the first irradiation angle range $AR_1$ on the basis of the overall imaging information acquired by the information acquisition unit 60 in Step S104 and sets the specified first irradiation angle range $AR_1$ as the irradiation angle range in the mammography apparatus 10. In a case in which the process in Step S106 ends, the imaging control process illustrated in FIG. 8 ends. Therefore, in the mammography apparatus 10, the radiation source 29 is moved to each of the irradiation positions $80_1$ to $80_{13}$, and the tomosynthesis imaging in the first irradiation angle range $AR_1$ is performed to capture the projection images $84_1$ to $84_{13}$.

Figure 7:
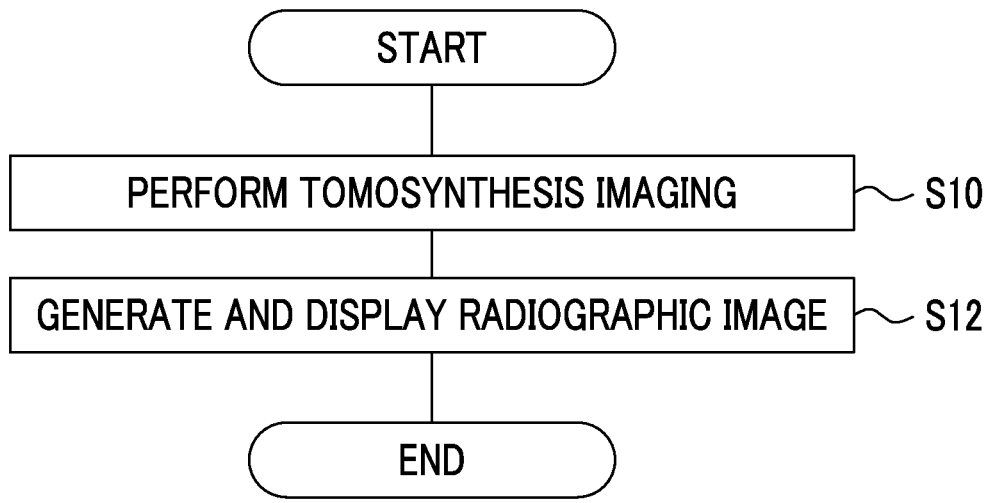
FIG. 7 is a flowchart illustrating an example of the flow of the tomosynthesis imaging.
Figure 8:
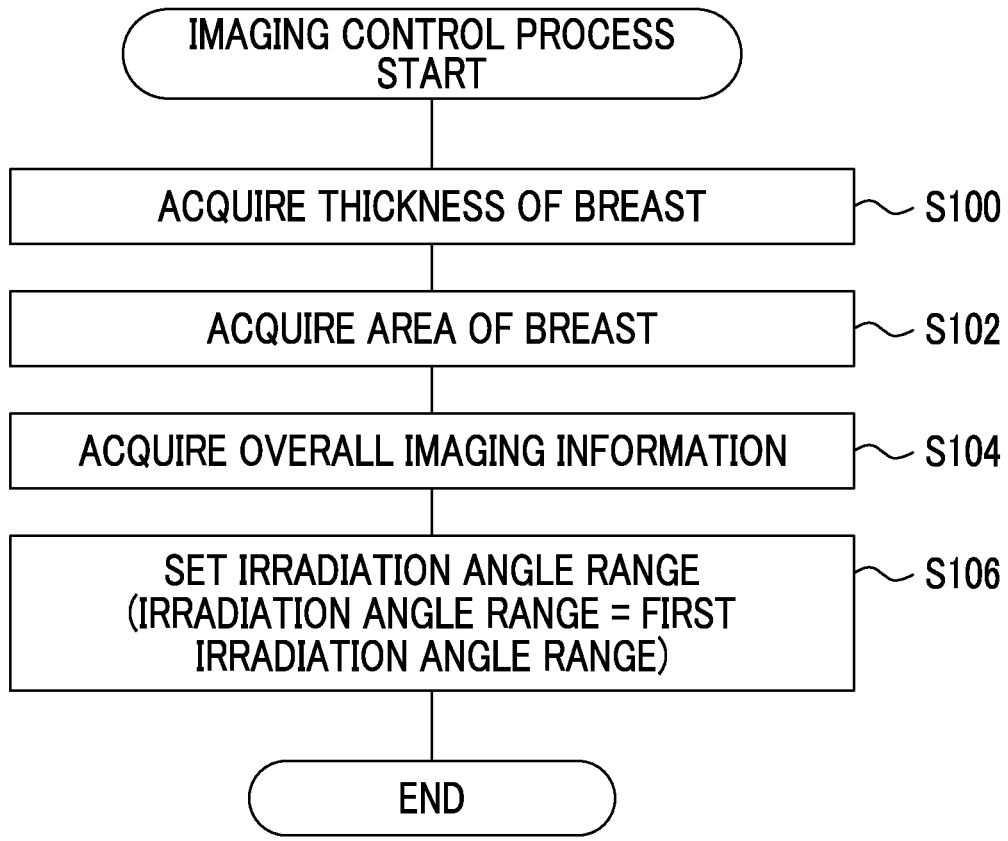
FIG. 8 is a flowchart illustrating an example of the flow of an imaging control process by the console according to the embodiment.

In a case in which the tomosynthesis imaging by the mammography apparatus 10 ends, the generation and display of various radiographic images by the console 12 in Step S12 of FIG. 7 are performed. The operation of the console 12 in the generation and display of various radiographic images will be described.

For example, in a case in which the tomosynthesis imaging ends, the mammography apparatus 10 according to this embodiment outputs the image data of the captured projection image group to the console 12. The console 12 stores the image data of the projection image group input from the mammography apparatus 10 in the storage unit 52.

Figure 9:
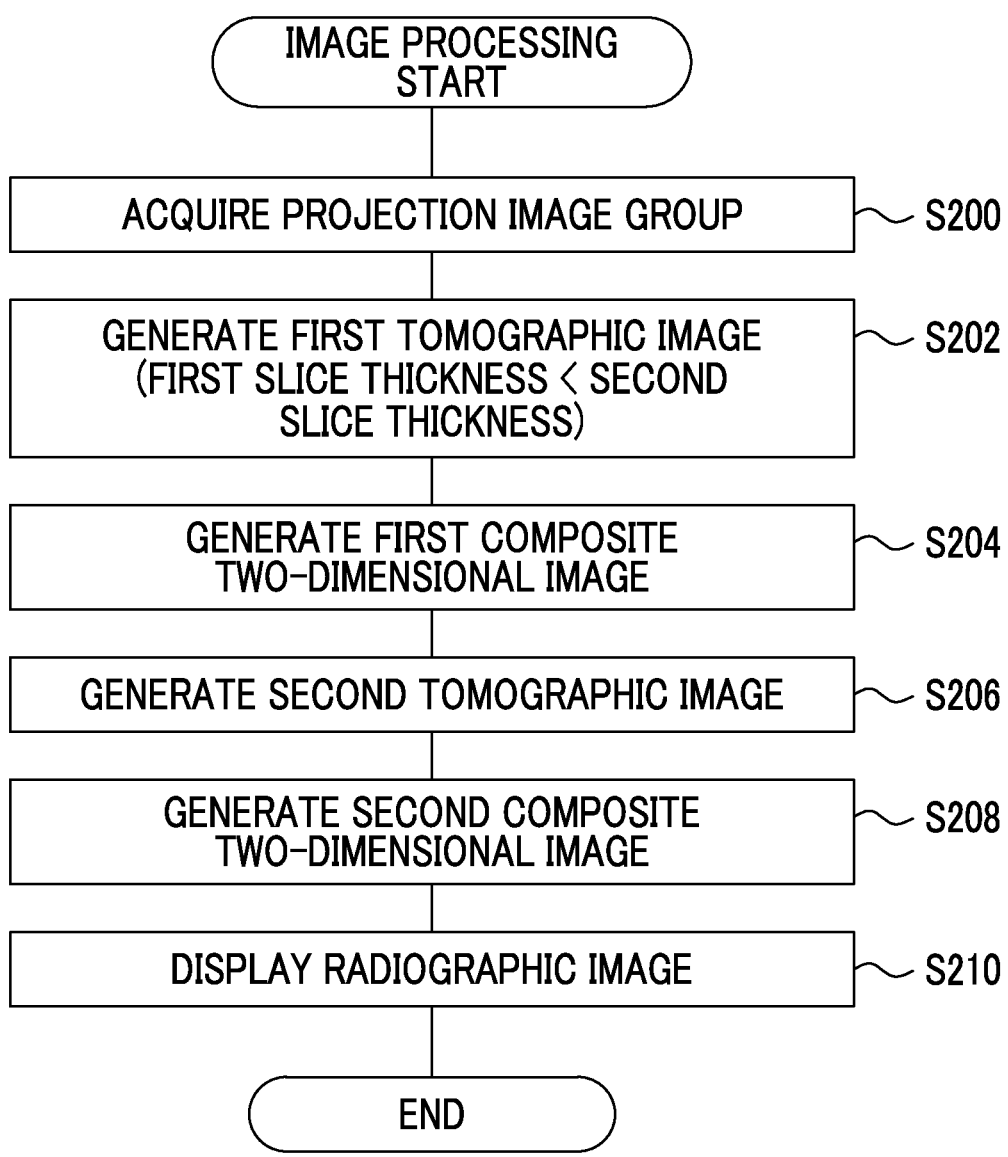
FIG. 9 is a flowchart illustrating an example of the flow of image processing by the console according to the embodiment.

After storing the image data of the projection image group in the storage unit 52, the console 12 performs image processing illustrated in FIG. 9. FIG. 9 is a flowchart illustrating an example of the flow of the image processing performed by the console 12 according to this embodiment. In the console 12 according to this embodiment, for example, the CPU 50A of the control unit 50 executes the image generation program 51B stored in the ROM 50B to perform the image processing whose example is illustrated in FIG. 9.

In Step S200 of FIG. 9, the image acquisition unit 64 acquires the projection image group. As described above, the image acquisition unit 64 according to this embodiment acquires, as the projection image group, the projection images $84_1$ to $84_{13}$ obtained by the tomosynthesis imaging in the first irradiation angle range $AR_1$ as the irradiation angle range wider than the overall imaging irradiation angle range $AR_a$ corresponding to the overall imaging information input from the information acquisition unit 60.

Then, in Step S202, the first tomographic image generation unit 66 generates the first tomographic image $86_1$. As described above, the first tomographic image generation unit 66 according to this embodiment generates a plurality of first tomographic images $86_1$ including a part of the object with the first slice thickness, using the plurality of projection images $84_1$ to $84_{13}$ obtained by the tomosynthesis imaging in the first irradiation angle range $AR_1$ among the projection images included in the projection image group acquired in Step S200.

Then, in Step S204, the first composite two-dimensional image generation unit 68 generates the first composite two-dimensional image. As described above, the first composite two-dimensional image generation unit 68 according to this embodiment combines at least some of the plurality of first tomographic images $86_1$ generated in Step S202 to generate the first composite two-dimensional image.

Then, in Step S206, the second tomographic image generation unit 70 generates the second tomographic image $86_2$. As described above, the second tomographic image generation unit 70 according to this embodiment generates a plurality of second tomographic images $86_2$ including the entire object, using a plurality of projection images $84_5$ to $84_9$ obtained by the tomosynthesis imaging in the second irradiation angle range $AR_2$ among the projection images included in the projection image group acquired in Step S200.

Then, in Step S208, the second composite two-dimensional image generation unit 72 generates the second composite two-dimensional image. As described above, the second composite two-dimensional image generation unit 72 according to this embodiment combines at least some of the plurality of second tomographic images $86_2$ generated in Step S206 to generate the second composite two-dimensional image.

Then, in Step S210, the display control unit 74 displays various radiographic images. Specifically, the display control unit 74 performs control to display the plurality of first tomographic image $86_1$ generated in Step S202, the first composite two-dimensional image generated in Step S204, the plurality of second tomographic images $86_2$ generated in Step S206, and the second composite two-dimensional image generated in Step S208 on the display unit 58.

Figure 10A:
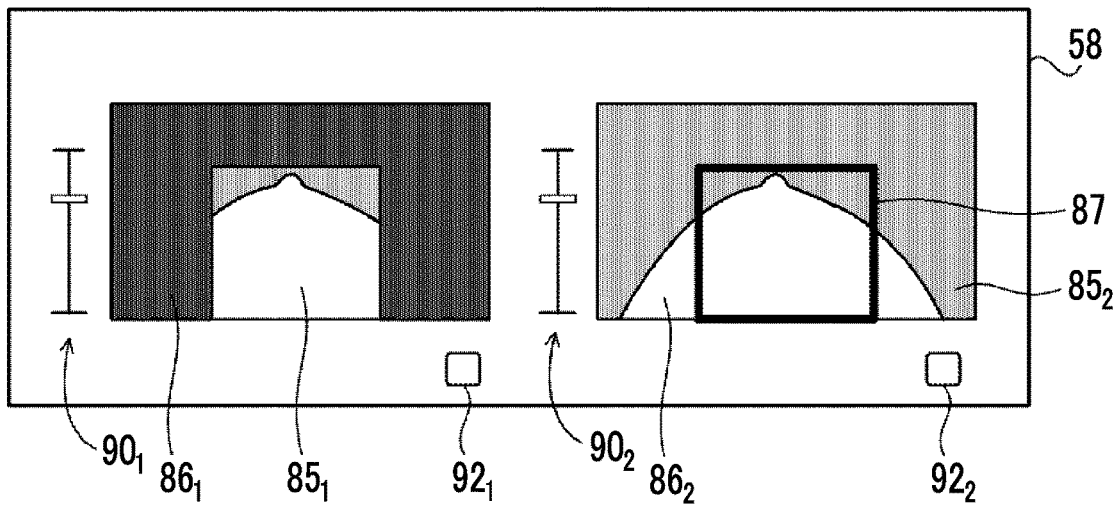
FIG. 10A is a diagram illustrating an example of a state in which a first tomographic image and a second tomographic image are displayed on a display unit.

For example, first, the display control unit 74 according to this embodiment displays the first tomographic image $86_1$ and the second tomographic image $86_2$ side by side on the display unit 58. FIG. 10A illustrates an example of a state in which the first tomographic image $86_1$ and the second tomographic image $86_2$ are displayed on the display unit 58. As illustrated in FIG. 10A, one first tomographic image $86_1$ and a slider bar $90_1$ are displayed on the display unit 58. In a case in which the user operates the operation unit 56 to move a bar of the slider bar $90_1$ along a slider, the first tomographic image $86_1$ having a height corresponding to the position of the bar is displayed on the display unit 58. Further, the second tomographic image $86_2$ and a slider bar $90_2$ are displayed on the display unit 58. In a case in which the user operates the operation unit 56 to move a bar of the slider bar $90_2$ along a slider, the second tomographic image $86_2$ having a height corresponding to the position of the bar is displayed on the display unit 58. In addition, the display control unit 74 according to this embodiment performs control to align the tomographic planes of the first tomographic image $86_1$ and the second tomographic image $86_2$ displayed on the display unit 58. In other words, the display control unit 74 performs control to align the heights of the first tomographic image $86_1$ and the second tomographic image $86_2$ displayed on the display unit 58. Therefore, in a case in which the user operates either the slider bar $90_1$ or the slider bar $90_2$ to change the height of either the first tomographic image $86_1$ or the second tomographic image $86_2$ displayed on the display unit 58, the height of the other of the first tomographic image $86_1$ and the second tomographic image $86_2$ displayed on the display unit 58 is also changed. Further, unlike this embodiment, the tomographic planes of the first tomographic image $86_1$ and the second tomographic image $86_2$ displayed on the display unit 58 may be different from each other, or a configuration that enables the user to switch whether or not to align the tomographic planes may be used.

Furthermore, as illustrated in FIG. 10A, in a case in which the first tomographic image $86_1$ is displayed, the display control unit 74 according to this embodiment displays reconstructed region information 87 indicating the reconstructed region $85_1$ of the first tomographic image $86_1$ so as to be superimposed on the first tomographic image $86_1$. This display of the reconstructed region information 87 indicating the reconstructed region $85_1$ on the first tomographic image $86_1$ makes it easy for the user to compare the first tomographic image $86_1$ with the second tomographic image $86_2$. In addition, the reconstructed region information 87 according to this embodiment is an example of information indicating a range of an object according to the present disclosure.

Figure 10B:
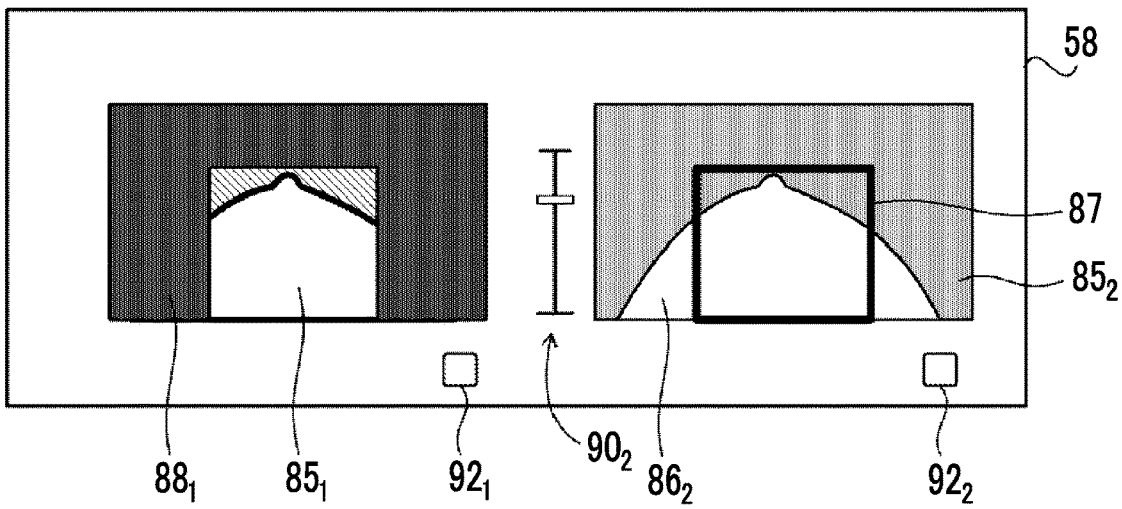
FIG. 10B is a diagram illustrating an example of a state in which a first composite two-dimensional image and the second tomographic image are displayed on the display unit.
Figure 10C:
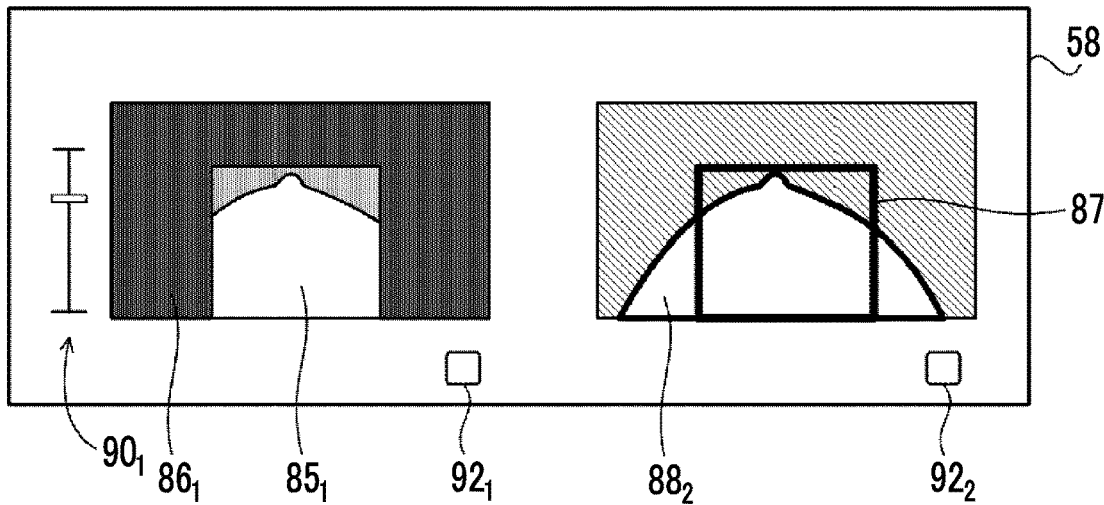
FIG. 10C is a diagram illustrating an example of a state in which the first tomographic image and a second composite two-dimensional image are displayed on the display unit.

Further, as illustrated in FIG. 10A, the display control unit 74 according to this embodiment displays switching buttons $92_1$ and $92_2$ on the display unit 58. In a case in which the operation of the switching button $92_1$ by the user through the operation unit 56 is received, the display control unit 74 performs control to switch the radiographic image displayed on the display unit 58 from one of the first tomographic image $86_1$ and the first composite two-dimensional image $88_1$ to the other. In a case in which the user operates the switching button $92_1$ in the state illustrated in FIG. 10A, the first composite two-dimensional image $88_1$ is displayed on the display unit 58 instead of the first tomographic image $86_1$, as illustrated in FIG. 10B. On the other hand, in a case in which the operation of the switching button $92_2$ by the user through the operation unit 56 is received, the display control unit 74 performs control to switch the radiographic image displayed on the display unit 58 from one of the second tomographic image $86_2$ and the second composite two-dimensional image $88_2$ to the other. In a case in which the user operates the switching button $92_2$ in the state illustrated in FIG. 10A, the second composite two-dimensional image $88_2$ is displayed on the display unit 58 instead of the second tomographic image $86_2$, as illustrated in FIG. 10C. In the example illustrated in FIG. 10C, the reconstructed region information 87 is displayed on the second composite two-dimensional image $88_2$. This display of the reconstructed region information 87 on the second composite two-dimensional image $88_2$ makes it easy for the user to compare the first tomographic image $86_1$ or the first composite two-dimensional image $88_1$ with the second composite two-dimensional image $88_2$.

In a case in which the process in Step S210 ends in this way, the image processing illustrated in FIG. 9 ends.

As described above, the console 12 according to the above-described embodiment is used in the mammography apparatus 10 performing the tomosynthesis imaging which irradiates the breast with the radiation R emitted from the radiation source 29 at each of the plurality of irradiation positions 80 having different irradiation angles to capture the projection images 84 of the breast at each of the irradiation positions 80. The console 12 comprises the CPU 50A as at least one processor. The CPU 50A acquires a projection image group including a plurality of projection images 84 obtained by the tomosynthesis imaging in an irradiation angle range wider than the overall imaging irradiation angle range $AR_a$ in which the tomographic image 86 including the entire breast can be obtained in a case in which the tomographic image 86 is generated using the projection images 84 obtained at each of the plurality of irradiation positions 80. The CPU 50A generates a plurality of first tomographic images $86_1$ including a part of the breast, using a plurality of projection images $84_1$ to $84_{13}$ obtained by the tomosynthesis imaging in the first irradiation angle range $AR_1$ wider than the overall imaging irradiation angle range $AR_a$ among the projection images 84 included in the projection image group. The CPU 50A generates a plurality of first tomographic images $86_1$ including the entire breast, using a plurality of projection images $84_5$ to $84_9$ obtained by the tomosynthesis imaging in the second irradiation angle range $AR_2$ which is equal to or narrower than the overall imaging irradiation angle range $AR_a$ among the projection images 84 included in the projection image group.

As described above, the console 12 according to the above-described embodiment generates two types of tomographic images 86 from the projection image group obtained by the tomosynthesis imaging in an irradiation angle range wider than the overall imaging irradiation angle range $AR_a$. The first tomographic image 86 is the first tomographic image $86_1$ corresponding to the tomosynthesis imaging in the first irradiation angle range $AR_1$ wider than the overall imaging irradiation angle range $AR_a$. Since the first irradiation angle range $AR_1$ is wider than the overall imaging irradiation angle range $AR_a$, the first tomographic image $86_1$ is an image in which a part of the object is included, but is a high-resolution image. The second tomographic image 86 is the second tomographic image $86_2$ corresponding to the tomosynthesis imaging in the second irradiation angle range $AR_2$ that is equal to or narrower than the overall imaging irradiation angle range $AR_a$. Since the second irradiation angle range $AR_2$ is equal to or narrower than the overall imaging irradiation angle range $AR_a$, the second tomographic image $86_2$ has a lower resolution than the first tomographic image $86_1$, but is an image in which the entire object is included.

Therefore, the console 12 according to the above-described embodiment can generate a high-resolution tomographic image and a tomographic image including the entire object from the projection image group including a plurality of projection images obtained by the tomosynthesis imaging in the irradiation angle range in which the entire object is not included in the tomographic image in a case in which the tomographic image is generated using all of the projection images.

Further, in the above-described embodiment, the tomosynthesis imaging in the first irradiation angle range $AR_1$ and the tomosynthesis imaging in the second irradiation angle range $AR_2$ can be performed by one tomosynthesis imaging operation. Therefore, even in an aspect in which the tomosynthesis imaging in the first irradiation angle range $AR_1$ and the tomosynthesis imaging in the second irradiation angle range $AR_2$ are performed separately, that is, an aspect in which the tomosynthesis imaging is performed twice, it is possible to reduce the time until two tomosynthesis imaging operations end. In addition, the movement of the object can be suppressed by suppressing the time until imaging ends.

In this embodiment, "one tomosynthesis imaging operation" means at least tomosynthesis imaging that is performed with the breast compressed by the compression plate 38. Therefore, the one tomosynthesis imaging operation also includes a case in which, after the tomosynthesis imaging in the first irradiation angle range $AR_1$ is performed with the breast compressed by the compression plate 38, the tomosynthesis imaging in the second irradiation angle range $AR_2$ is performed with the breast compressed by the compression plate 38. Alternatively, the "one tomosynthesis imaging" means tomosynthesis imaging that is performed from the start of the capture of the projection image 84 at the irradiation position 80 defined as a start position to the end of the capture of the projection image 84 at the irradiation position 80 defined as an end position by, for example, the imaging menu.

Figure 11:
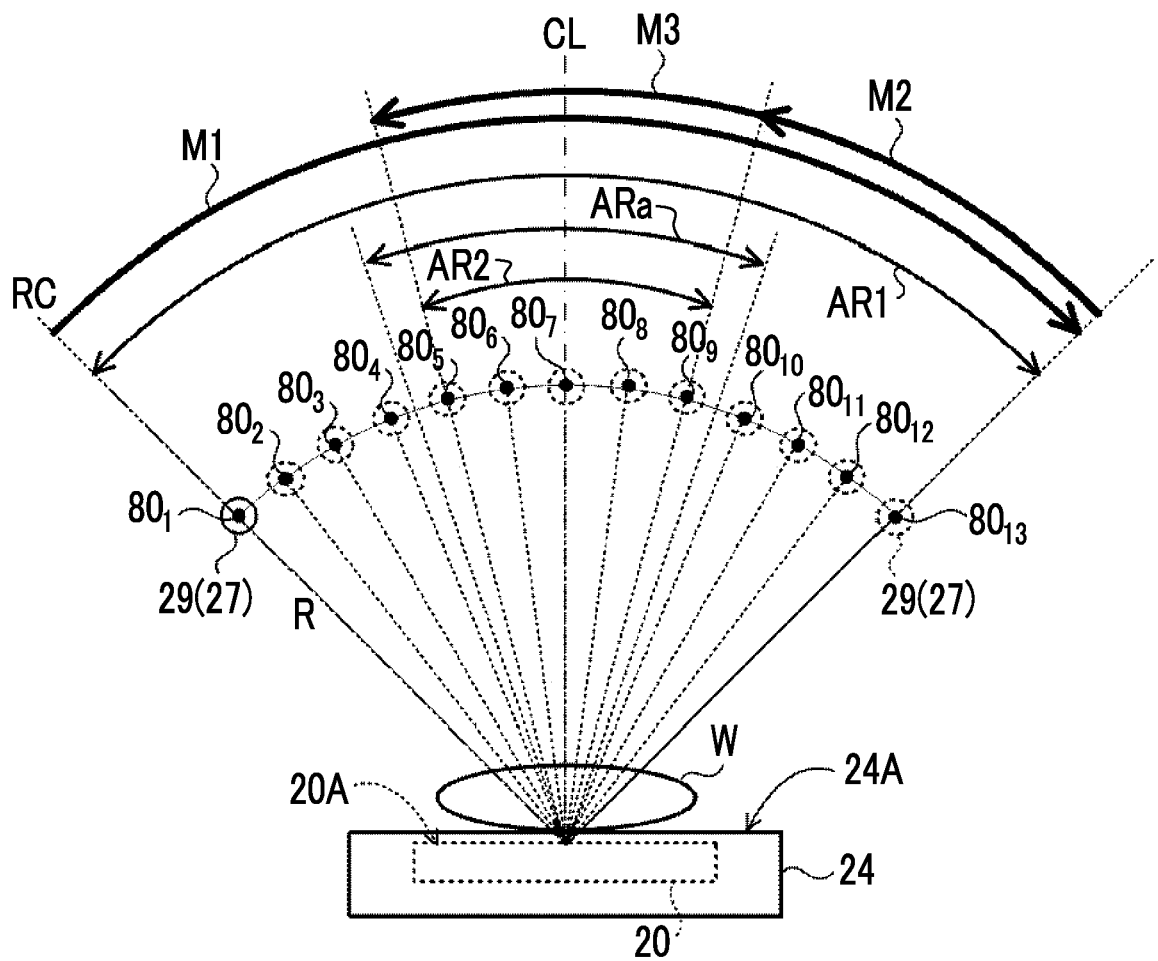
FIG. 11 is a diagram illustrating one tomosynthesis imaging operation in the embodiment.

For one tomosynthesis imaging operation, an example different from the above-mentioned aspect will be described with reference to FIG. 11. First, the breast W is compressed by the compression plate 38 (not illustrated in FIG. 11), the radiation source 29 is moved from the irradiation position $80_1$ defined as the start position to the irradiation position $80_{13}$ in a movement direction M1, and the tomosynthesis imaging in the first irradiation angle range $AR_1$ is performed. Then, the radiation source 29 is moved from the irradiation position $80_{13}$ to the irradiation position $80_9$ in a movement direction M2 in a state in which the breast W is compressed by the compression plate 38. In a case in which the radiation source 29 reaches the irradiation position $80_9$, the radiation source 29 is moved from the irradiation position $80_9$ to the irradiation position $80_5$ defined as the end position in a movement direction M3 in a state in which the breast W is compressed, and the tomosynthesis imaging in the second irradiation angle range $AR_2$ is performed. As described above, two types of tomosynthesis imaging are performed in a state in which the breast W is compressed by the compression plate 38. Therefore, it is possible to suppress the movement of the breast due to body movement during each tomosynthesis imaging operation.

Further, in the above-described embodiment, the projection images $84_5$ to $84_9$ obtained by the tomosynthesis imaging in the first irradiation angle range $AR_1$ are used as the projection images $84_5$ to $84_9$ obtained by the tomosynthesis imaging in the second irradiation angle range $AR_2$. As described above, the console 12 according to the above-described embodiment uses one projection image 84 to generate the first tomographic image $86_1$ and the second tomographic image $86_2$. Therefore, it is possible to reduce the number of times the projection image 84 is captured in the entire tomosynthesis imaging and to shorten the time related to the entire tomosynthesis imaging until the two types of tomosynthesis imaging end.

In addition, in the above-described embodiment, the aspect in which projection images $84_5$ to $84_9$ obtained at the irradiation positions $80_5$ to $80_9$ in the second irradiation angle range $AR_2$ are used to generate both the first tomographic image $86_1$ and the second tomographic image $86_2$ has been described. However, the present disclosure is not limited to this aspect. Each of the projection images $84_5$ to $84_9$ may be used to generate either the first tomographic image $86_1$ or the second tomographic image $86_2$. For example, the irradiation positions $80_6$ and $80_8$ may be used to generate the first tomographic image $86_1$, and the irradiation positions $80_5$, $80_7$, and $80_9$ may be used to generate the second tomographic image $86_2$. In other words, the irradiation positions 80 in the first irradiation angle range $AR_1$ may be the irradiation positions $80_1$ to $80_4$, $80_6$, $80_8$, and $80_{10}$ to $80_{13}$, and the irradiation positions 80 in the second irradiation angle range $AR_2$ may be the irradiation positions $80_5$, $80_7$, and $80_9$.

Figure 12:
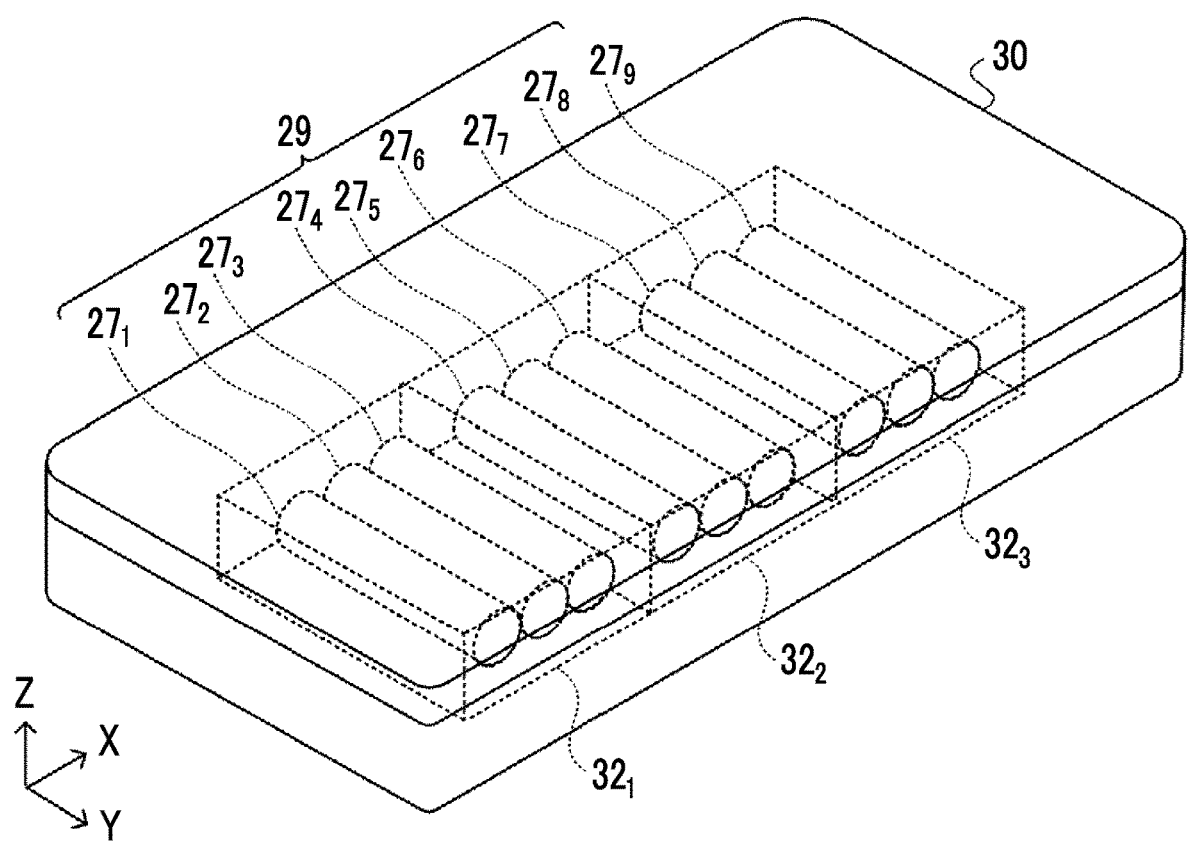
FIG. 12 is a diagram illustrating an example of a radiation source including a plurality of radiation tubes.

Further, in the above-described embodiment, the aspect in which the radiation source 29 of the mammography apparatus 10 comprises one radiation tube 27 and is moved to each irradiation position 80 to perform the tomosynthesis imaging has been described. However, the radiation source 29 comprising a plurality of radiation tubes 27 may be used, and the tomosynthesis imaging may be performed without moving the radiation source 29. FIG. 12 illustrates an example of the radiation source 29 comprising the plurality of radiation tubes 27. In addition, FIG. 12 illustrates the radiation source 29 comprising nine radiation tubes 27. However, the number of radiation tubes 27 comprised in the radiation source 29 is not limited to this aspect. The nine radiation tubes 27 are divided such that three radiation tubes 27 are accommodated in each of three housings $32_1$ to $32_3$. The three housings $32_1$ to $32_3$ are disposed in the radiation emitting unit 28 in a state of being accommodated in a radiation source accommodation portion 30.

In a case in which the mammography apparatus 10 performs the tomosynthesis imaging, the radiation source 29 of the radiation emitting unit 28 sequentially emits radiation at each of the plurality of irradiation positions having different irradiation angles. The radiation source 29 includes a plurality of radiation tubes 27, and each of the plurality of radiation tubes 27 is disposed at the irradiation positions 80.

Figure 13:
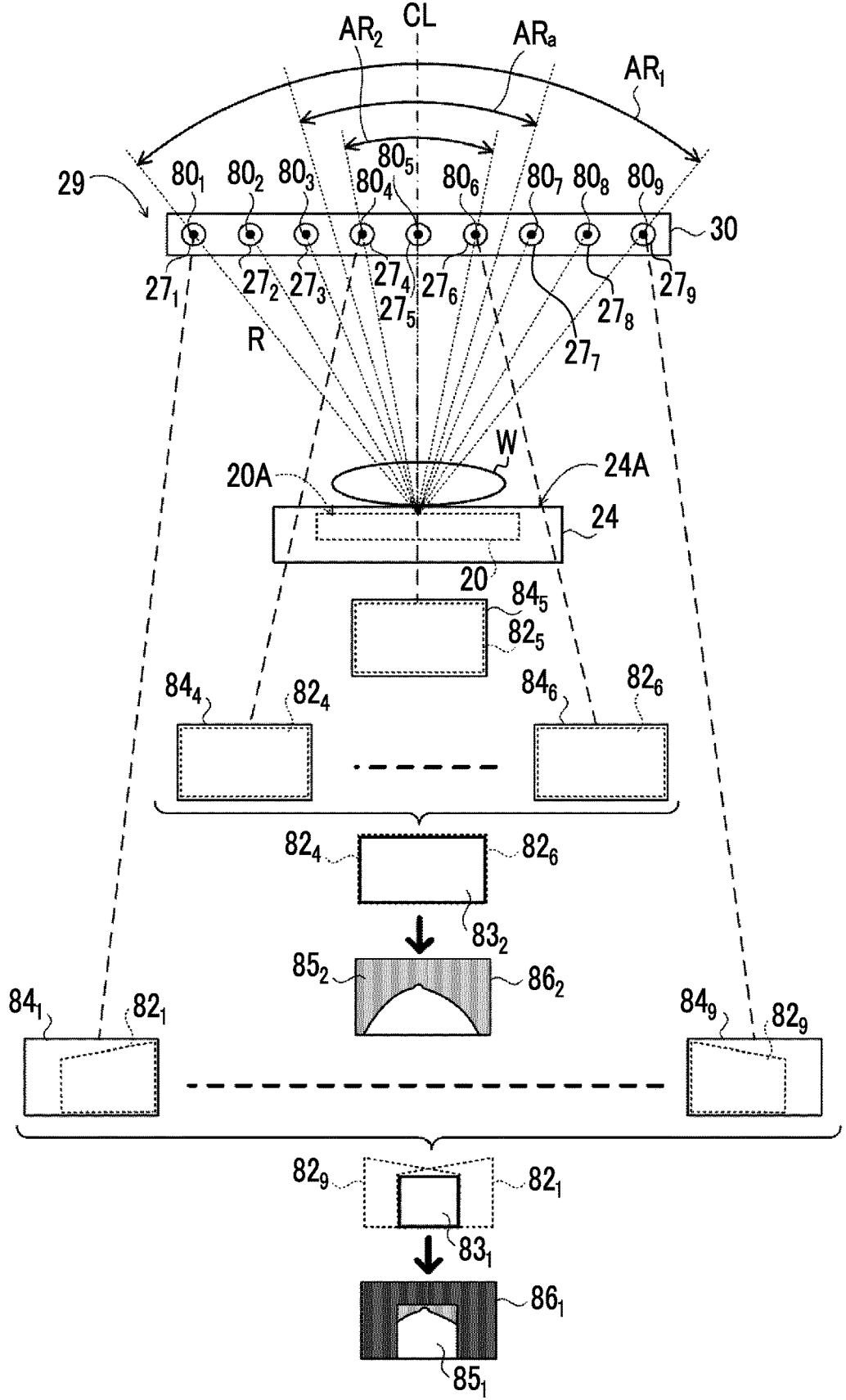
FIG. 13 is a diagram illustrating an example of the tomosynthesis imaging performed using the radiation source illustrated in FIG. 12.

FIG. 13 is a diagram illustrating an example of the tomosynthesis imaging performed using the radiation source 29 illustrated in FIG. 12. In addition, the compression plate 38 is not illustrated in FIG. 13. In this embodiment, as illustrated in FIG. 13, the radiation tubes $27_1$ to $27_j$ (j=2, . . . , the maximum value is 9 in FIG. 13) of the radiation source 29 are disposed at predetermined irradiation positions $80_j$. In other words, in the example illustrated in FIG. 13, the radiation tubes $27_1$ to $27_9$ are disposed at the irradiation positions $80_1$ to $80_9$ where the radiation R is incident on the detection surface 20A of the radiation detector 20 at different angles. At each of the irradiation positions $80_1$ to $80_9$, the radiation R is sequentially emitted from the radiation source 29 to the breast W in response to an instruction from the console 12, and the radiation detector 20 captures projection images. In the radiography system 1, the radiation R is sequentially emitted from the radiation tubes $27_1$ to $27_9$ to sequentially capture the projection images $84_1$ to $84_9$. In the example illustrated in FIG. 13, nine projection images are obtained.

In a case in which the irradiation angle range is the first irradiation angle range $AR_1$ wider than the overall imaging irradiation angle range $AR_a$, a partial region $83_1$ common to object regions $82_1$ to $82_9$ included in projection images $84_1$ to $84_9$ obtained at each of the irradiation positions $80_1$ to $80_9$ corresponds to a reconstructed region $85_1$ in a case in which a first tomographic image $86_1$ is generated. The partial region $83_1$, that is, the reconstructed region $85_1$ is smaller than the object regions $82_1$ to $82_9$ included in the projection images $84_1$ to $84_9$. Therefore, in this aspect, the first tomographic image $86_1$ is an image in which a part of the object is included. For example, FIG. 13 illustrates the first tomographic image $86_1$ in which a part of the breast W, which is the object, is included.

Since the first irradiation angle range $AR_1$ is wider than the overall imaging irradiation angle range $AR_a$, the first tomographic image $86_1$ generated using a plurality of first projection images $84_1$ to $84_9$ obtained by the tomosynthesis imaging in the first irradiation angle range $AR_1$ is a high-resolution image.

On the other hand, in a case in which the irradiation angle range is equal to or narrower than the overall imaging irradiation angle range $AR_a$, the reconstructed region 85 in the tomographic image 86 is equivalent to the object region $82_5$. Therefore, the tomographic image 86 is an image in which the entire object is included.

In a case in which the irradiation angle range is the second irradiation angle range $AR_2$, a partial region $83_2$ common to the object regions $82_4$ to $82_6$ included in the projection images $84_4$ to $84_6$ obtained at each of the irradiation positions $80_4$ to $80_6$ corresponds to a reconstructed region $85_2$ in a case in which a second tomographic image $86_2$ is generated. The partial region $83_2$, that is, the reconstructed region $85_2$ is equivalent to the object regions $82_4$ to $82_6$ included in the projection images $84_4$ to $84_6$. Therefore, in this embodiment, the second tomographic image $86_2$ is an image in which the entire object is included. For example, FIG. 13 illustrates the second tomographic image $86_2$ in which the entire breast W, which is the object, is included.

As described above, in a case in which the radiation source 29 includes the plurality of radiation tubes 27 and each of the plurality of radiation tubes 27 is disposed at the irradiation positions 80, it is possible to perform the tomosynthesis imaging without moving the radiation source 29, that is, the radiation tubes 27 to each irradiation position 80. In addition, in the example illustrated in FIG. 13, the aspect in which the radiation tubes $27_1$ to $27_9$ are arranged in a straight line has been described. However, the specific arrangement of the radiation tubes $27_1$ to $27_9$ is not limited to this aspect. For example, the radiation tubes $27_1$ to $27_9$ may be disposed in a state in which the axes connecting the focuses of the radiation tubes $27_1$ to $27_9$ and a preset position, such as the center of the detection surface 20A, have the same length. In this case, since the positions where the radiation tubes $27_1$ to $27_9$ are disposed are the irradiation positions 80, the radiation tubes $27_1$ to $27_9$ are disposed so as to draw an arc like the irradiation positions $80_1$ to $80_{13}$ illustrated in FIG. 2.

Further, in the above-described embodiment, the aspect in which the console 12 is an example of the image processing device and the imaging control device according to the present disclosure has been described. However, devices other than the console 12 may have the functions of the image processing device and the imaging control device according to the present disclosure. In other words, a device, such as the mammography apparatus 10 or an external device, other than the console 12 may have some or all of the functions of the information acquisition unit 60, the irradiation angle range control unit 62, the image acquisition unit 64, the first tomographic image generation unit 66, the first composite two-dimensional image generation unit 68, the second tomographic image generation unit 70, the second composite two-dimensional image generation unit 72, and the display control unit 74. In addition, in the above-described embodiment, the aspect in which one device has the functions of the image processing device and the imaging control device has been described. However, different devices may have the functions of the image processing device and the imaging control device. Further, for example, a device other than the console 12 or a plurality of devices including the console 12 may have some or all of the functions of the image processing device and the imaging control device.

In addition, in the above-described embodiment, the aspect in which the breast is applied as an example of the object according to the present disclosure and the mammography apparatus 10 is applied as an example of the radiography apparatus according to the present disclosure has been described. However, the object is not limited to the breast, and the radiography apparatus is not limited to the mammography apparatus. For example, the object may be the chest, the abdomen, or the like, and radiography apparatuses other than the mammography apparatus may be applied.

Further, in the above-described embodiment, for example, the following various processors can be used as the hardware structure of processing units performing various processes such as the information acquisition unit 60, the irradiation angle range control unit 62, the image acquisition unit 64, the first tomographic image generation unit 66, the first composite two-dimensional image generation unit 68, the second tomographic image generation unit 70, the second composite two-dimensional image generation unit 72, and the display control unit 74. The various processors include, for example, a programmable logic device (PLD), such as a field programmable gate array (FPGA), that is a processor whose circuit configuration can be changed after manufacture and a dedicated electric circuit, such as an application specific integrated circuit (ASIC), that is a processor having a dedicated circuit configuration designed to perform a specific process, in addition to the CPU that is a general-purpose processor which executes software (programs) to function as various processing units as described above.

One processing unit may be configured by one of the various processors or a combination of two or more processors of the same type or different types (for example, a combination of a plurality of FPGAs or a combination of a CPU and an FPGA). Further, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). As described above, various processing units are configured using one or more of the various processors as a hardware structure.

In addition, specifically, an electric circuit (circuitry) obtained by combining circuit elements, such as semiconductor elements, can be used as the hardware structure of the various processors.

Further, in the above-described embodiment, the aspect in which the imaging program 41 is stored (installed) in the ROM 40B in advance, and the imaging control program 51A and the image generation program 51B are stored (installed) in the ROM 50B in advance has been described. However, the present disclosure is not limited thereto. The imaging program 41, the imaging control program 51A, and the image generation program 51B may be recorded on a recording medium, such as a compact disc read only memory (CD-ROM), a digital versatile disc read only memory (DVD-ROM), or a universal serial bus (USB) memory, and then provided. Further, each of the imaging program 41, the imaging control program 51A, and the image generation program 51B may be downloaded from an external device through a network.

What is claimed is:

1. An image processing device that is used in a radiography apparatus performing tomosynthesis imaging which irradiates an object with radiation emitted from a radiation source at each of a plurality of irradiation positions having different irradiation angles to capture projection images of the object at each of the irradiation positions, the image processing device comprising:
   at least one processor,
   wherein the processor acquires a projection image group including a plurality of projection images obtained by the tomosynthesis imaging in an irradiation angle range wider than an overall imaging irradiation angle range in which a tomographic image including an entire object is obtainable in a case in which the tomographic image is generated using the projection images obtained at each of the plurality of irradiation positions, generates a plurality of first tomographic images including a part of the object, using a plurality of projection images obtained by the tomosynthesis imaging in a first irradiation angle range wider than the overall imaging irradiation angle range among the projection images included in the projection image group, and generates a plurality of second tomographic images including the entire object, using a plurality of projection images obtained by the tomosynthesis imaging in a second irradiation angle range that is equal to or narrower than the overall imaging irradiation angle range among the projection images included in the projection image group.

2. The image processing device according to claim 1, wherein the processor acquires a plurality of projection images obtained by one tomosynthesis imaging operation as the projection image group.

3. The image processing device according to claim 1, wherein the processor generates the plurality of second tomographic images using some of the plurality of projection images used to generate the first tomographic images.

4. The image processing device according to claim 1, wherein the processor displays the first tomographic image and the second tomographic image side by side.

5. The image processing device according to claim 1, wherein the processor displays information indicating a range of the object included in the first tomographic image so as to be superimposed on the second tomographic image.

6. The image processing device according to claim 1, wherein the processor generates at least one of a first composite two-dimensional image obtained by combining at least some of the plurality of first tomographic images or a second composite two-dimensional image obtained by combining at least some of the plurality of second tomographic images and displays at least one of the plurality of first tomographic images or the first composite two-dimensional image and at least one of the plurality of second tomographic images or the second composite two-dimensional image side by side.

7. The image processing device according to claim 1, wherein the processor generates a second composite two-dimensional image obtained by combining at least some of the plurality of second tomographic images and displays information indicating a range of the object included in the first tomographic image so as to be superimposed on the second composite two-dimensional image.

8. The image processing device according to claim 1, wherein the processor sets a slice thickness of the plurality of first tomographic images to be smaller than a slice thickness of the plurality of second tomographic images.

9. The image processing device according to claim 1, wherein the processor acquires overall imaging information indicating the overall imaging irradiation angle range which is determined on the basis of at least one of a thickness of the object or an area of the object and specifies the second irradiation angle range on the basis of the acquired overall imaging information.

10. The image processing device according to claim 9, wherein the object is a breast that is placed on an imaging table and is compressed by a compression member, and the area of the object is a contact area of the breast with the imaging table or a contact area of the breast with the compression member.

11. The image processing device according to claim 1, wherein the radiation source includes a plurality of radiation tubes that are disposed at each of the plurality of irradiation positions and generate the radiation, and the radiography apparatus sequentially generates the radiation from the plurality of radiation tubes to perform the tomosynthesis imaging.

12. The image processing device according to claim 1, wherein the radiation source includes a radiation tube that generates the radiation, and the radiography apparatus moves the radiation source to the plurality of irradiation positions to perform the tomosynthesis imaging.

13. An imaging control device that is used in a radiography apparatus performing tomosynthesis imaging which irradiates an object with radiation emitted from a radiation source at each of a plurality of irradiation positions having different irradiation angles to capture projection images of the object at each of the irradiation positions, the imaging control device comprising:
at least one processor,
wherein the processor acquires overall imaging information indicating an overall imaging irradiation angle range determined on the basis of at least one of a thickness of the object or an area of the object and controls the radiography apparatus such that the tomosynthesis imaging is performed in an irradiation angle range wider than the overall imaging irradiation angle range corresponding to the acquired overall imaging information.

14. A radiography system comprising:
a radiation source that generates radiation;
a radiography apparatus that performs tomosynthesis imaging which irradiates an object with the radiation emitted from the radiation source at each of a plurality of irradiation positions having different irradiation angles to capture projection images of the object at each of the irradiation positions; and
the image processing device according to claim 1.

15. An image processing method that is executed by a computer and is used in a radiography apparatus performing tomosynthesis imaging which irradiates an object with radiation emitted from a radiation source at each of a plurality of irradiation positions having different irradiation angles to capture projection images of the object at each of the irradiation positions, the image processing method comprising:
acquiring a projection image group including a plurality of projection images obtained by the tomosynthesis imaging in an irradiation angle range wider than an overall imaging irradiation angle range in which a tomographic image including an entire object is obtainable in a case in which the tomographic image is generated using the projection images obtained at each of the plurality of irradiation positions;
generating a plurality of first tomographic images including a part of the object, using a plurality of projection images obtained by the tomosynthesis imaging in a first irradiation angle range wider than the overall imaging irradiation angle range among the projection images included in the projection image group; and
generating a plurality of second tomographic images including the entire object, using a plurality of projection images obtained by the tomosynthesis imaging in a second irradiation angle range that is equal to or narrower than the overall imaging irradiation angle range among the projection images included in the projection image group.

16. A non-transitory computer-readable storage medium storing an image processing program that is used in a radiography apparatus performing tomosynthesis imaging which irradiates an object with radiation emitted from a radiation source at each of a plurality of irradiation positions having different irradiation angles to capture projection images of the object at each of the irradiation positions, the image processing program causing a computer to perform a process comprising:
acquiring a projection image group including a plurality of projection images obtained by the tomosynthesis imaging in an irradiation angle range wider than an overall imaging irradiation angle range in which a tomographic image including an entire object is obtainable in a case in which the tomographic image is generated using the projection images obtained at each of the plurality of irradiation positions;
generating a plurality of first tomographic images including a part of the object, using a plurality of projection images obtained by the tomosynthesis imaging in a first irradiation angle range wider than the overall imaging irradiation angle range among the projection images included in the projection image group; and
generating a plurality of second tomographic images including the entire object, using a plurality of projection images obtained by the tomosynthesis imaging in a second irradiation angle range that is equal to or narrower than the overall imaging irradiation angle range among the projection images included in the projection image group.

* * * * *